(12) United States Patent
Kahle et al.

(10) Patent No.: US 8,721,658 B2
(45) Date of Patent: May 13, 2014

(54) TISSUE RETRIEVAL SYSTEM

(75) Inventors: Henry Kahle, Trabuco Canyon, CA (US); Gary M Johnson, Mission Viejo, CA (US); Scott V. Taylor, Mission Viejo, CA (US); Gregory I Bak-Boychuck, Laguna Niguel, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 771 days.

(21) Appl. No.: 11/549,971

(22) Filed: Oct. 16, 2006

(65) Prior Publication Data

US 2007/0088370 A1 Apr. 19, 2007

Related U.S. Application Data

(60) Provisional application No. 60/726,821, filed on Oct. 14, 2005.

(51) Int. Cl.
*A61B 17/24* (2006.01)

(52) U.S. Cl.
USPC .......................................... 606/114

(58) Field of Classification Search
USPC .................. 606/113, 114, 110, 115, 127, 128
See application file for complete search history.

(56) References Cited

U.S. PATENT DOCUMENTS

| 30,471 | A | 10/1860 | Dudley |
|---|---|---|---|
| 1,609,014 | A | 11/1926 | Dowd |
| 3,476,114 | A | 11/1969 | Shannon et al. |
| 3,476,115 | A | 11/1969 | Graeff et al. |
| 4,287,807 | A * | 9/1981 | Pacharis et al. .................. 411/42 |
| 4,428,375 | A | 1/1984 | Ellman |
| 4,732,150 | A | 3/1988 | Keener, Jr. |
| 4,741,335 | A * | 5/1988 | Okada ........................... 606/127 |
| 4,991,593 | A | 2/1991 | LeVahn |
| 5,037,379 | A | 8/1991 | Clayman et al. |
| 5,074,867 | A | 12/1991 | Wilk |
| 5,143,082 | A | 9/1992 | Kindberg et al. |

(Continued)

FOREIGN PATENT DOCUMENTS

| DE | 25796 | 1/1884 |
|---|---|---|
| DE | 4216165 | 11/1992 |

(Continued)

OTHER PUBLICATIONS

European Patent Office, International Search Report and Written Opinion of the International Searching Authority for International Application No. PCT/US2006/060022, mailed Jun. 5, 2007.

(Continued)

*Primary Examiner* — Kathleen Holwerda
*Assistant Examiner* — Sarah Simpson
(74) *Attorney, Agent, or Firm* — John F. Heal; David G. Majdali

(57) ABSTRACT

The tissue retrieval system deploys a tissue bag at the surgical site. The bag is supported by the system as tissue is placed within the bag and is closed to isolate the collected tissue and allow the bag and collected tissue to be removed from the body. The bag can be reopened and re-closed as desired through use of a guide bead and cord. The bead also facilitates removal of the collected tissue.

22 Claims, 23 Drawing Sheets

(56) References Cited

U.S. PATENT DOCUMENTS

| | | |
|---|---|---|
| 5,147,371 A | 9/1992 | Washington et al. |
| 5,176,687 A | 1/1993 | Hasson et al. |
| 5,190,542 A | 3/1993 | Nakao et al. |
| 5,190,555 A | 3/1993 | Wetter et al. |
| 5,190,561 A | 3/1993 | Graber |
| 5,192,284 A | 3/1993 | Pleatman |
| 5,192,286 A | 3/1993 | Phan et al. |
| 5,195,507 A | 3/1993 | Bilweis |
| 5,201,740 A | 4/1993 | Nakao et al. |
| 5,215,521 A | 6/1993 | Cochran et al. |
| 5,234,439 A | 8/1993 | Wilk et al. |
| 5,279,539 A | 1/1994 | Bohan et al. |
| 5,279,548 A | 1/1994 | Essig et al. |
| 5,308,327 A | 5/1994 | Heaven et al. |
| 5,312,416 A | 5/1994 | Spaeth et al. |
| 5,336,227 A | 8/1994 | Nakao et al. |
| 5,337,754 A | 8/1994 | Heaven et al. |
| 5,341,815 A * | 8/1994 | Cofone et al. .............. 600/562 |
| 5,352,184 A | 10/1994 | Goldberg et al. |
| 5,354,303 A | 10/1994 | Spaeth et al. |
| 5,366,460 A | 11/1994 | Eberbach |
| 5,368,597 A | 11/1994 | Pagedas |
| 5,417,684 A | 5/1995 | Jackson et al. |
| 5,417,697 A | 5/1995 | Wilk et al. |
| 5,465,731 A | 11/1995 | Bell et al. |
| 5,480,404 A | 1/1996 | Kammerer et al. |
| 5,486,182 A | 1/1996 | Nakao et al. |
| 5,486,183 A | 1/1996 | Middleman et al. |
| RE35,164 E | 3/1996 | Kindberg et al. |
| 5,509,923 A | 4/1996 | Middleman et al. |
| 5,524,633 A * | 6/1996 | Heaven et al. .............. 600/562 |
| 5,535,759 A | 7/1996 | Wilk |
| 5,601,572 A | 2/1997 | Middleman et al. |
| 5,611,803 A | 3/1997 | Heaven et al. |
| 5,613,973 A | 3/1997 | Jackson et al. |
| 5,632,746 A | 5/1997 | Middleman et al. |
| 5,643,283 A * | 7/1997 | Younker .................. 606/17 |
| 5,647,372 A * | 7/1997 | Tovey et al. .............. 600/562 |
| 5,655,657 A | 8/1997 | Roshdy |
| 5,656,012 A | 8/1997 | Sienkiewicz |
| 5,679,423 A | 10/1997 | Shah |
| 5,681,324 A * | 10/1997 | Kammerer et al. .......... 606/113 |
| 5,720,754 A | 2/1998 | Middleman et al. |
| 5,735,289 A | 4/1998 | Pfeffer et al. |
| 5,741,271 A | 4/1998 | Nakao et al. |
| 5,749,879 A | 5/1998 | Middleman et al. |
| 5,759,187 A * | 6/1998 | Nakao et al. ............... 606/114 |
| 5,779,716 A | 7/1998 | Cano et al. |
| 5,782,839 A | 7/1998 | Hart et al. |
| 5,785,677 A | 7/1998 | Auweiler |
| 5,809,621 A | 9/1998 | McCree et al. |
| 5,820,628 A | 10/1998 | Middleman et al. |
| 5,853,374 A | 12/1998 | Hart et al. |
| 5,904,690 A | 5/1999 | Middleman et al. |
| 5,947,978 A * | 9/1999 | Holsinger .................. 606/110 |
| 5,971,995 A * | 10/1999 | Rousseau .................. 606/114 |
| 5,980,544 A | 11/1999 | Vaitekunas |
| 5,997,547 A | 12/1999 | Nakao et al. |
| 6,004,330 A | 12/1999 | Middleman et al. |
| 6,015,415 A | 1/2000 | Avellanet |
| 6,019,770 A | 2/2000 | Christoudias |
| 6,059,793 A | 5/2000 | Pagedas |
| 6,206,889 B1 * | 3/2001 | Bennardo .................. 606/127 |
| 6,228,095 B1 | 5/2001 | Dennis |
| 6,258,102 B1 | 7/2001 | Pagedas |
| 6,264,663 B1 * | 7/2001 | Cano ...................... 606/114 |
| 6,350,267 B1 | 2/2002 | Stefanchik |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,419,639 B2 | 7/2002 | Walther et al. |
| 6,447,523 B1 | 9/2002 | Middleman et al. |
| 6,575,988 B2 | 6/2003 | Rousseau |
| 6,805,699 B2 | 10/2004 | Shimm |
| 6,814,739 B2 | 11/2004 | Secrest et al. |
| 6,958,069 B2 | 10/2005 | Shipp et al. |
| 6,986,774 B2 | 1/2006 | Middleman et al. |
| 7,041,055 B2 | 5/2006 | Young et al. |
| 7,115,125 B2 | 10/2006 | Nakao |
| 7,270,663 B2 | 9/2007 | Nakao |
| 7,547,310 B2 | 6/2009 | Whitfield |
| 7,618,437 B2 | 11/2009 | Nakao |
| 7,670,346 B2 | 3/2010 | Whitfield |
| 2003/0100919 A1 | 5/2003 | Hopkins |
| 2004/0087969 A1 * | 5/2004 | Kayan et al. .............. 606/110 |
| 2004/0097960 A1 | 5/2004 | Terachi et al. |
| 2004/0138587 A1 | 7/2004 | Lyons, IV |
| 2004/0158280 A1 * | 8/2004 | Morris et al. .............. 606/200 |
| 2004/0254573 A1 | 12/2004 | Dycus et al. |
| 2005/0165411 A1 | 7/2005 | Orban, III |
| 2005/0267489 A1 | 12/2005 | Secrest et al. |
| 2005/0267492 A1 | 12/2005 | Poncet et al. |
| 2005/0283186 A1 * | 12/2005 | Berrada et al. ............ 606/200 |
| 2006/0052799 A1 | 3/2006 | Middleman et al. |
| 2006/0173468 A1 * | 8/2006 | Simmon et al. ............. 606/113 |
| 2006/0200169 A1 | 9/2006 | Sniffin |
| 2006/0200170 A1 | 9/2006 | Aranyi |
| 2006/0229639 A1 | 10/2006 | Whitfield |
| 2006/0276805 A1 | 12/2006 | Yu |
| 2007/0088370 A1 | 4/2007 | Kahle et al. |
| 2008/0033451 A1 | 2/2008 | Rieber et al. |
| 2008/0221587 A1 | 9/2008 | Schwartz |
| 2008/0221588 A1 | 9/2008 | Hollis et al. |
| 2008/0234696 A1 | 9/2008 | Taylor et al. |
| 2009/0043315 A1 | 2/2009 | Moon |
| 2009/0082779 A1 | 3/2009 | Nakao |
| 2009/0192510 A1 | 7/2009 | Bahney |
| 2010/0076451 A1 | 3/2010 | Zwolinski et al. |
| 2010/0152609 A1 | 6/2010 | Zwolinski et al. |

FOREIGN PATENT DOCUMENTS

| | | |
|---|---|---|
| DE | 197 07 361 | 8/1998 |
| EP | 499243 A1 | 8/1992 |
| EP | 0 947 166 A2 | 10/1999 |
| JP | 5-115493 | 5/1993 |
| JP | 6-154161 | 6/1994 |
| SU | 1537229 | 4/1987 |
| WO | WO 93/15671 | 8/1993 |
| WO | WO 93/24063 | 12/1993 |
| WO | WO 94/13215 | 6/1994 |
| WO | WO 03/105674 | 12/2003 |
| WO | WO 2007/081601 | 7/2007 |

OTHER PUBLICATIONS

The International Bureau of WIPO, The International Preliminary Report on Patentability for International Application No. PCT/US2006/060022, mailed Jul. 24, 2008.

United States Surgical, Tyco Healthcare Group LP, Autosuture* ENDO CATCH* Single-Use Specimen Pouch, Frequently Asked Questions and Features and Benefits (Web pages), 2004 4 pages.

United States Surgical, Tyco Healthcare Group LP, Autosuture* ENDOCATCH* Gold 10 mm Single-Use Specimen Pouch 10000-25912, Product Information Data Sheet Feb. 2004, 2 pages.

United States Surgical, Tyco Healthcare Group LP, Autosuture* ENDOCATCH* II Single-Use Specimen Pouch, 10000-19724, Product Information Data Sheet, Aug. 2002, 2 pages.

CONMED Corporation, EndoSurgery Products, Hand Held Laparoscopic Instruments, Product Descriptions (Web pages), 2004, 3 pages.

Cook Group Inc., Cook Urological, Cook® Drainage Pouch Sets, Product Description (Web page), 2003, 1 page.

Johnson & Johnson Gateway LLC, Ethicon Endo-Surgery Inc., Endoscopic Product Family, ENDOPOUCH Retriever Specimen Retrieval Bag Product Description (Web Page) 2000-2005 1 page.

The International Bureau of WIPO, The International Preliminary Report on Patentability for International Application No. PCT/US2006/060007 mailed Apr. 24, 2008.

European Patent Office, International Search Report and Written Opinion of the International Searching Authority for International Application No. PCT/US2006/060007 mailed Mar. 2, 2007.

(56) References Cited

OTHER PUBLICATIONS

Co-Pending U.S. Appl. No. 11/549,701, filed Oct. 16, 2006; Title: Device for Isolating and Removing Tissue From a Body Cavity, and it's associated file history.

Co-Pending U.S. Appl. No. 12/902,055, filed Oct. 11, 2010; Title: Single Incision Laparoscopic Tissue Retrieval System, and it's associated file history.

Co-Pending U.S. Appl. No. 11/549,971, filed Oct. 16, 2006; Title: Tissue Retrieval System, and its associated file history.

Co-Pending U.S. Appl. No. 13/252,110, filed Oct. 3, 2011; Title: Laparoscopic Tissue Retrieval System, and its associated file history.

U.S. Appl. No. 5,853,374, filed Oct. 11, 1995, (now abandoned), entitled "Tissue Collection and Retrieval Bag", and its associated file history.

International Search Report and Written Opinion for International Application No. PCT/US2010/052190, mailed Feb. 3, 2011.

The International Bureau of WIPO, International Preliminary Report on Patentability, for International Application No. PCT/US2010/052190, entitled Single Incision Laparoscopic Tissue Retrieval System, mailed Apr. 11, 2012.

International Searching Authority, The International Search Report and Written Opinion for International Application No. PCT/US2011/054647,entitled Laparoscopic Tissue Retrieval System, dated Feb. 21, 2012.

* cited by examiner

TISSUE RETRIEVAL SYSTEM

CROSS-REFERENCE TO RELATED APPLICATIONS

This application claims the benefit of U.S. Provisional Application No. 60/726,821, filed Oct. 14, 2005, the disclosure of which is hereby incorporated by reference as if set forth in full herein.

BACKGROUND

This invention relates generally to apparatus and methods for capturing and retrieving tissue from body cavities and in particular to a specimen retrieval bag device.

Laparoscopic surgery is typically performed through trocars, which provide access across the abdominal wall and into the abdominal cavity. In some of surgeries, tissue disposed within the abdominal cavity is cut and removed from the body. However, removal of such tissue from the body may prove difficult due to the limited confines inherent with laparoscopic surgery and the available laparoscopic surgical instruments. Also, such tissue may include an infected or cancerous mass or organ, as well as blood, bile and other liquids, all referred to herein as tissue, which may pose infection issues or other complications if left within the body.

It is desirable to grasp, capture, retain and enclose this tissue while in the body cavity, and then remove the enclosed tissue through the trocar or incision. Containment of the tissue as quickly as possible with minimal disturbance to the surgical site is also desirable. A generally compact and single unit device would also prove desirable as devices generally bulky and complicated have several shortcomings and lack optimal efficiency in particular with the limited space in operating rooms and access ports in the body cavity.

SUMMARY

Generally, the present invention provides a tissue or specimen retrieval device. In one aspect, a tissue retrieval apparatus comprises an actuator and a tissue bag having an open end and a closed end. The open end of the tissue bag is connected to the actuator and a cord is attached along a periphery of the open end of the tissue bag and to the actuator. A guide bead frictionally coupled to the cord.

In one aspect, a tissue retrieval apparatus comprises an actuation rod movable in a proximal and a distal direction. A tissue bag is connected to the actuation rod and is movable from a stored position to a deployed position. A ratchet is connected to the actuation rod and is movable between a first and a second position. The ratchet in the first position is arranged to allow the bag to be moved from the stored position to the deployed position as the actuation rod is moved in the distal direction and restrict movement of the actuation rod in the proximal direction. The ratchet in the second position is arranged to allow the actuation rod to move in the proximal direction and restrict movement of the actuation rod in the distal direction.

In one aspect, a tissue retrieval apparatus comprises an introducer tube having a longitudinally extending lumen and a movable actuator having a proximal and a distal end and connected to the introducer tube and movable through the lumen of the introducer tube. The distal end of the actuator has at least one support arm and the proximal end of the actuator has a handle. A tissue bag has an open end and a closed end with the open end coupled to the at least one support arm. A cord attaches to the open end of the tissue bag and the movable actuator. The cord is a continuous closed loop.

In one aspect, a tissue retrieval apparatus comprises a cord, a tissue bag having an open end and a closed end with the open end attached to the cord; and a guide bead frictionally connected to the cord. In one aspect, a tissue retrieval apparatus comprises a cord and a tissue bag having an open end, a closed end and a superabsorbent polymer with the open end attached to the cord.

In one aspect, a tissue retrieval apparatus comprises an introducer tube having a longitudinally extending lumen with a handle assembly extending from one end of the introducer tube. The handle assembly has a pair of finger loops. The apparatus further comprises an actuation rod with a proximal and a distal end and is movable through the lumen and the distal end has a plurality of support arms and the proximal end has a handle. A tissue bag has an open end and a closed end with the open end releasably coupled to the support arms and having a continuous cord loop attached to the open end of the tissue bag and being releasably attached to the movable actuation rod. The apparatus further comprises a guide bead being substantially cylindrical with a bore and the cord loop extending through the bore and a pawl having at least one tooth and a rack having a plurality of teeth operationally engaging with the at least one tooth of the pawl. The rack is attached to the actuation rod and the pawl is pivotally attached to the handle assembly.

Many of the attendant features of the present invention will be more readily appreciated as the same becomes better understood by reference to the foregoing and following description and considered in connection with the accompanying drawings in which like reference symbols designate like parts throughout.

DETAILED DESCRIPTION

Figure 1:
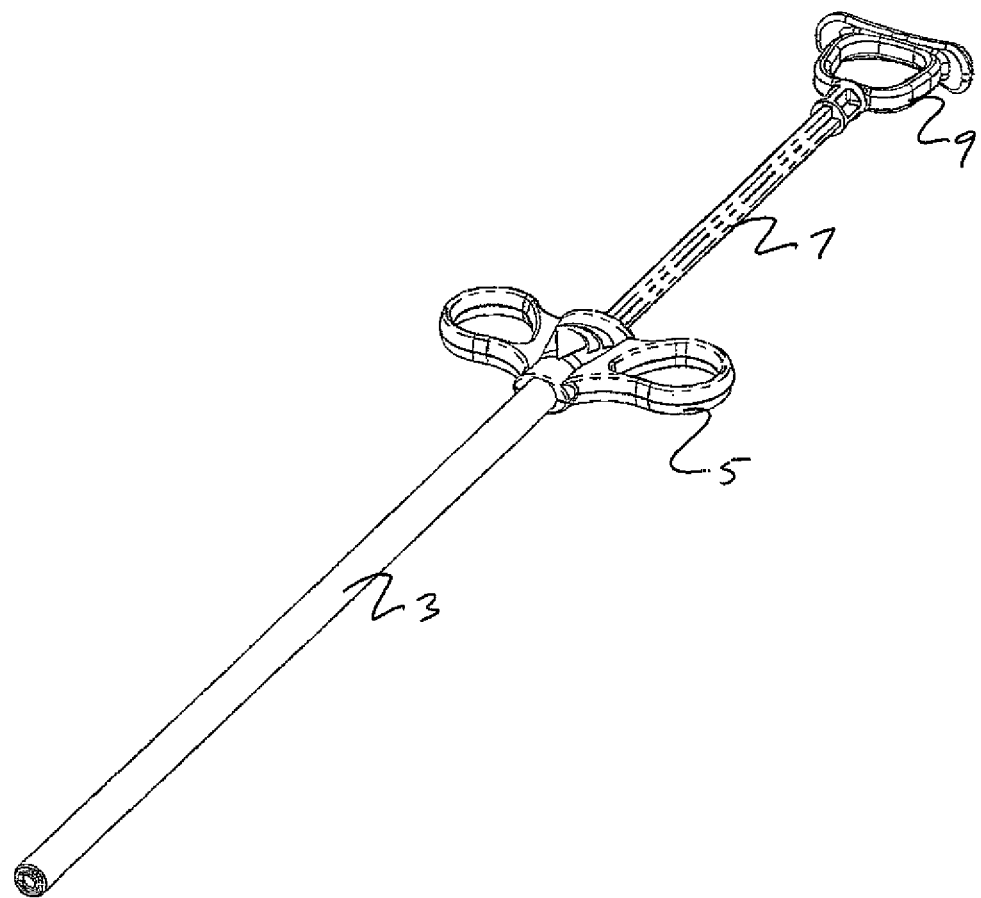
FIG. 1 is a perspective view of a tissue retrieval system in a non-deployed condition in accordance with various aspects of the present invention.

In this description, "proximal" or "proximally" refers to that portion of the instrument, component, or element that extends toward the user. "Distal" or "distally" refers to that portion of the instrument, component, or element that extends away from the user. In FIG. 1, a tissue retrieval device in a non-deployed or non-activated initial condition is shown. The tissue retrieval device is arranged to contain and withdraw excised tissue specimens from within a body cavity. The tissue retrieval device has an introducer 3 and an actuator or actuation rod 7. The introducer 3 in one aspect has a tubular configuration with a hollow lumen and a handle assembly 5 extending from a proximal end of the introducer. The handle assembly has a pair of finger loops or grips utilized to hold or stabilize the introducer as desired. The proximal end and/or the distal end of the introducer 3 in one aspect are generally open. The actuator rod 7 in one aspect has a handle 9 extending from a proximal end of the actuator rod 7. The handle 9 provides a graspable portion of the device to control or facilitate movement of the actuator rod relative to the introducer 3.

Figure 2:
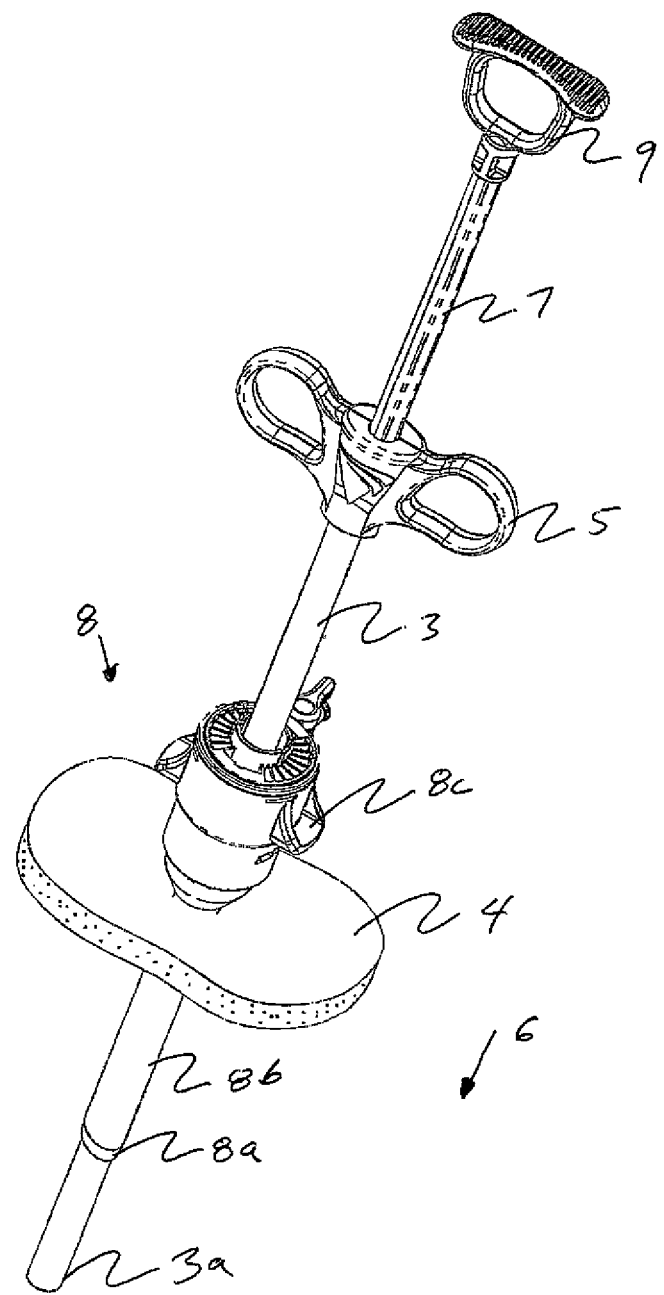
FIG. 2 is a perspective view of a tissue retrieval system positioned through an access port and a body wall in accordance with various aspects of the present invention.

Referring now to FIG. 2, operationally, an access device 8, such as a trocar, is first placed through a body wall 4 leaving an access conduit, e.g., the trocar cannula 8b, disposed across the body wall. Using the handle assembly 5 to maneuver the introducer 3, the tissue retrieval device is inserted into the conduit, e.g., through the trocar cannula 8b and/or a seal housing 8c attached to or included with the trocar cannula, until a distal end 3a of an introducer tube 3 extends beyond a distal end 8a of the trocar cannula 8b.

Figure 3:
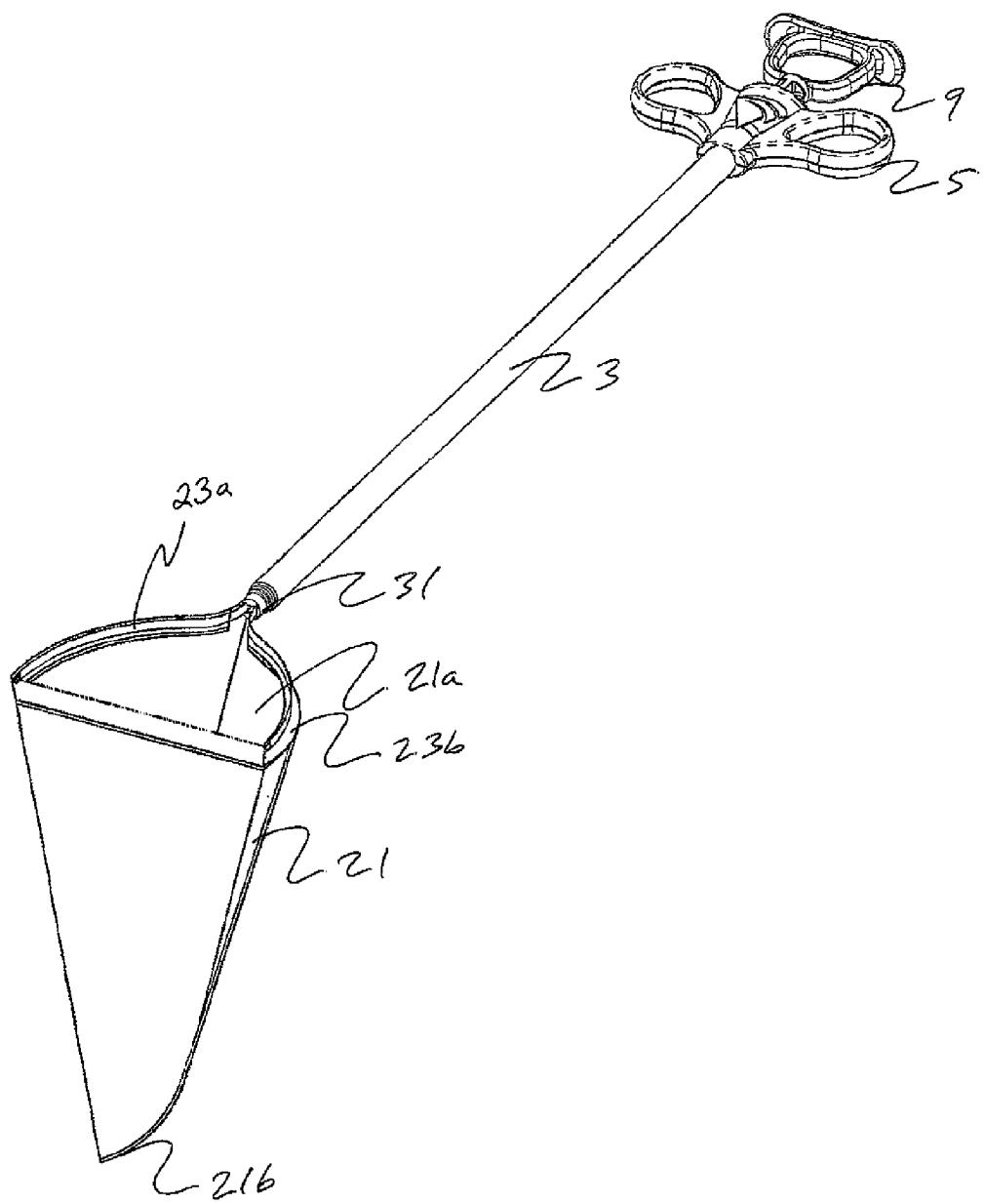
FIG. 3 is a perspective view of a tissue retrieval system in a deployed condition in accordance with various aspects of the present invention.

In FIG. 3, movement of the actuator rod 7 relative to the introducer tube 3 activates the deployment of a specimen bag 21, which is arranged as a receptacle for tissue specimens. In particular, the specimen bag 21 is deployed out from the introducer tube 3 and into the body cavity by pushing the actuation rod 7 in a distal direction as shown by arrow 6. Extended into the body cavity, the specimen bag 21 is suspended and held open by two support arms 23a,b extending from the actuation rod 7. Each support arm is attached to or integrated with the actuation rod 7. The specimen or tissue bag has an open end 21a, through which tissue specimens are inserted, to rest in a closed end 21b of the specimen bag. In one aspect, the specimen bag is a polyurethane specimen bag.

Figure 4:
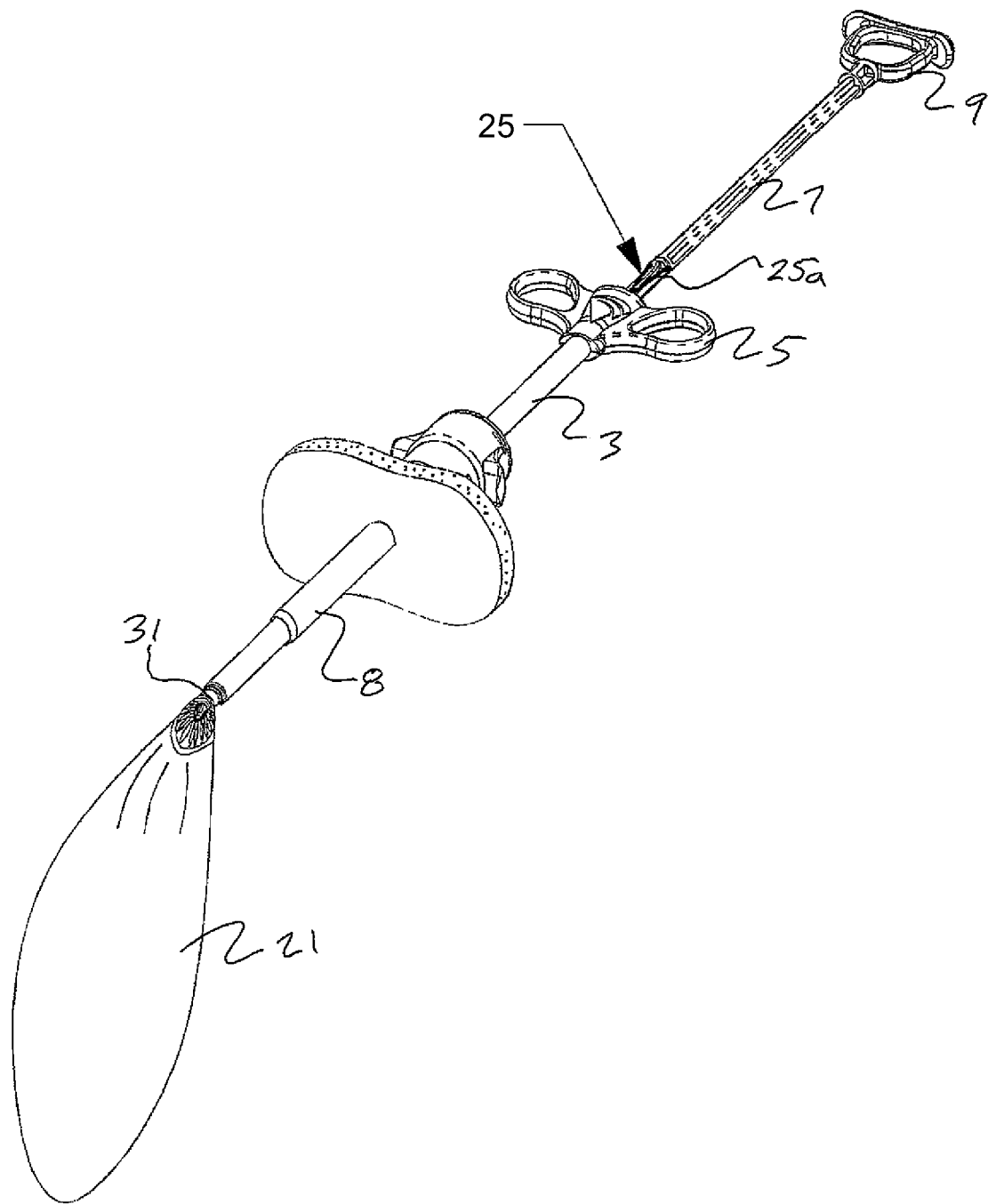
FIG. 4 is a perspective view of a tissue retrieval system with a specimen bag closed and the system positioned through an access port and a body wall in accordance with various aspects of the present invention.

Once a tissue specimen, such as a gallbladder or portions thereof, is separated from the adjoining vessels and structures, it is placed into the specimen bag 21. After insertion of the tissue specimens into the specimen bag 21, the specimen bag 21 in one aspect is closed to prevent spillage of its contents and to prevent contamination of the body cavity wall and/or other tissue in the body cavity during withdrawal of the tissue specimen from within the body cavity. Referring to FIG. 4, the actuation rod 7 is retracted proximally to withdraw the support arms 23a,b from the specimen bag 21 without disrupting or disturbing the bag or the contents within the bag. In one aspect, the support arms 23a,b are pulled out of or from the specimen bag and tension is applied to a cord loop 25 to cinch the bag 21 closed. In one aspect, a bead 31 is attached to the cord loop 25 engaging the bag 21 to assist in closing the bag 21. The guide bead is made of a material, e.g., polycarbonate, which is different from the material of the cord loop, e.g., nitinol. As such, the guide bead is less resilient than the cord and thereby provides and facilitates withdrawal of the bag, manipulation of the bag and opening/re-opening and closing/re-closing of the bag as discussed in greater detail below. Once the specimen bag is fully closed, a small loop end or portion 25a of the cord is exposed on the actuation rod 7 near the proximal end of the introducer 3 or handle assembly 5.

Figure 5:
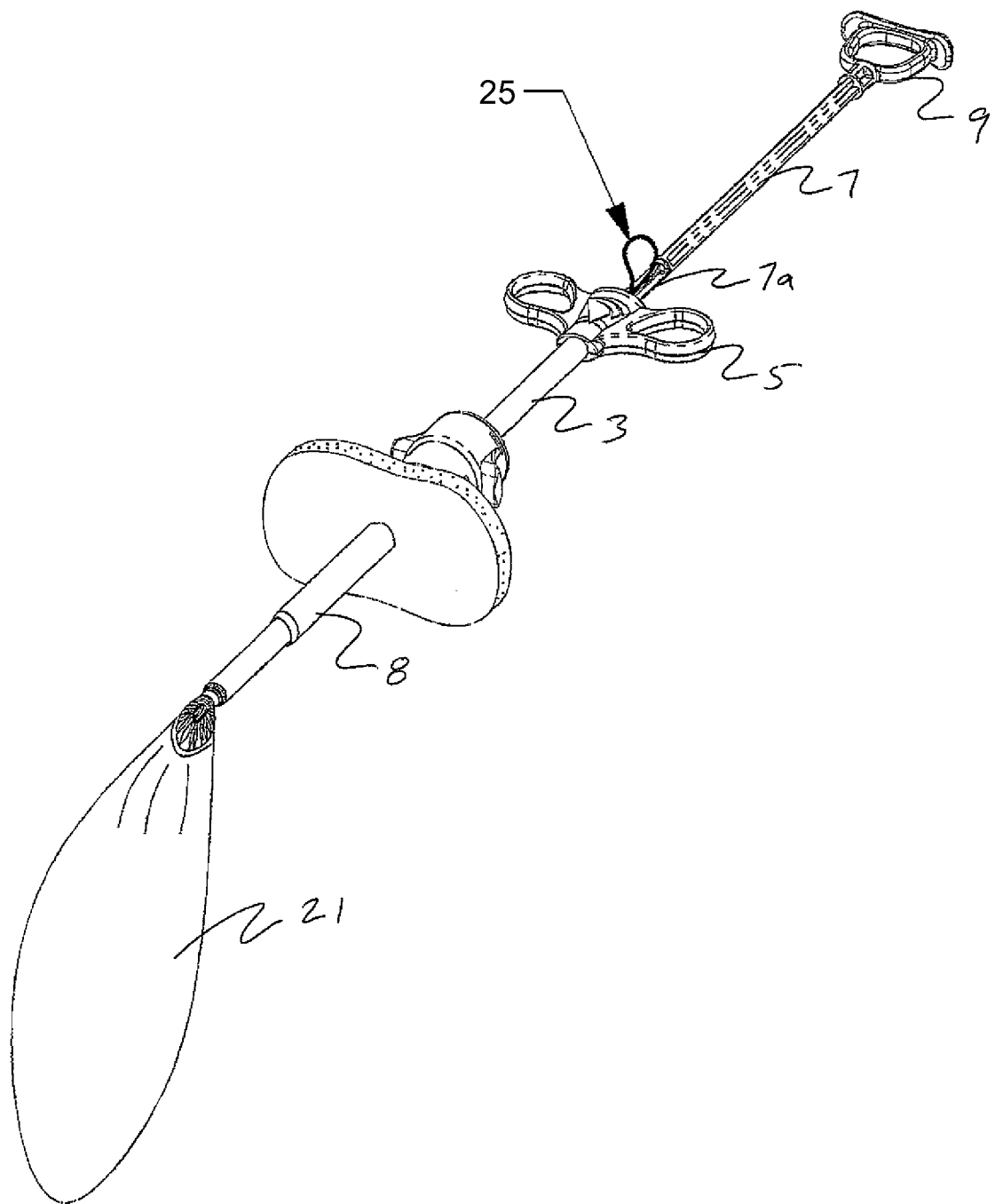
FIG. 5 is a perspective view of a tissue retrieval system with a specimen bag closed and the system positioned through an access port and a body wall with a cord loop detached in accordance with various aspects of the present invention.
Figure 6:
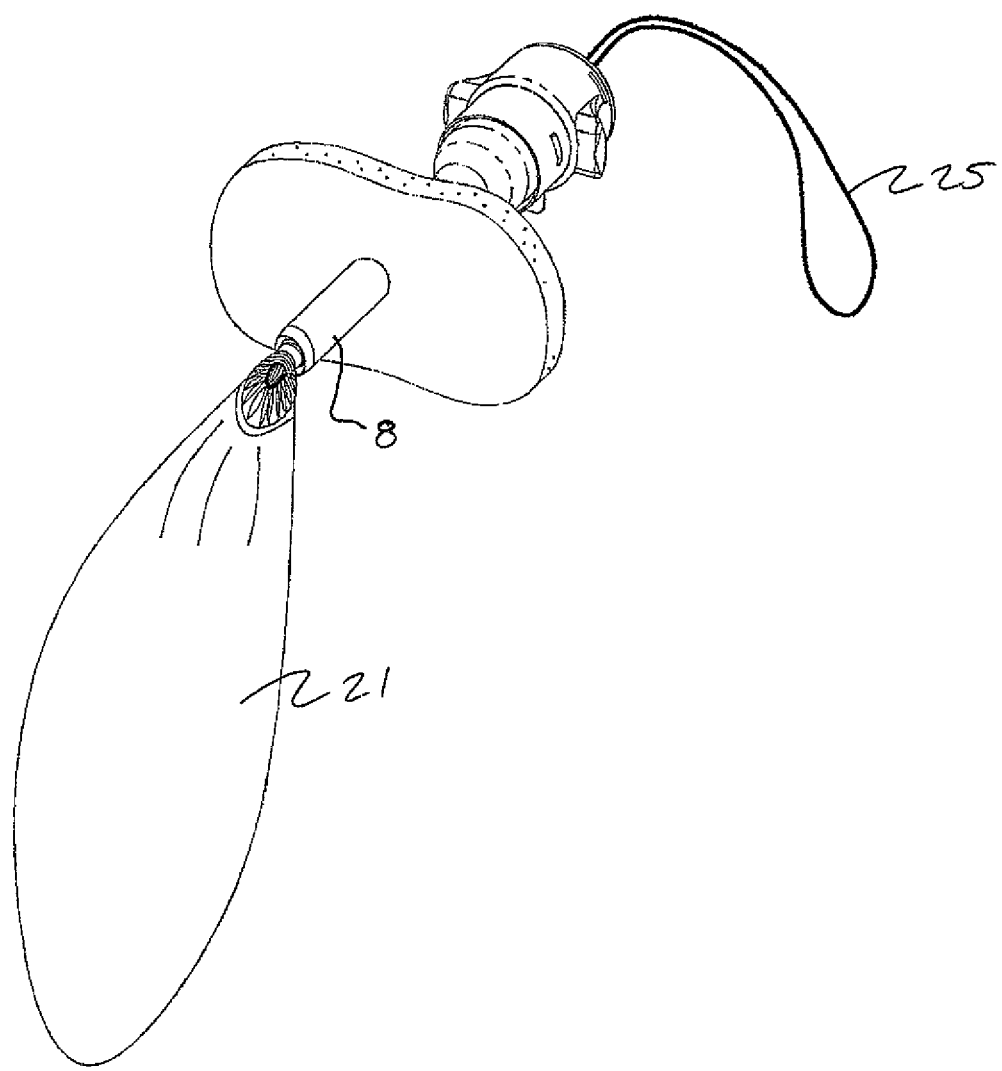
FIG. 6 is a perspective view of a tissue retrieval system with the removal of an introducer and actuation assembly in accordance with various aspects of the present invention.
Figure 7:
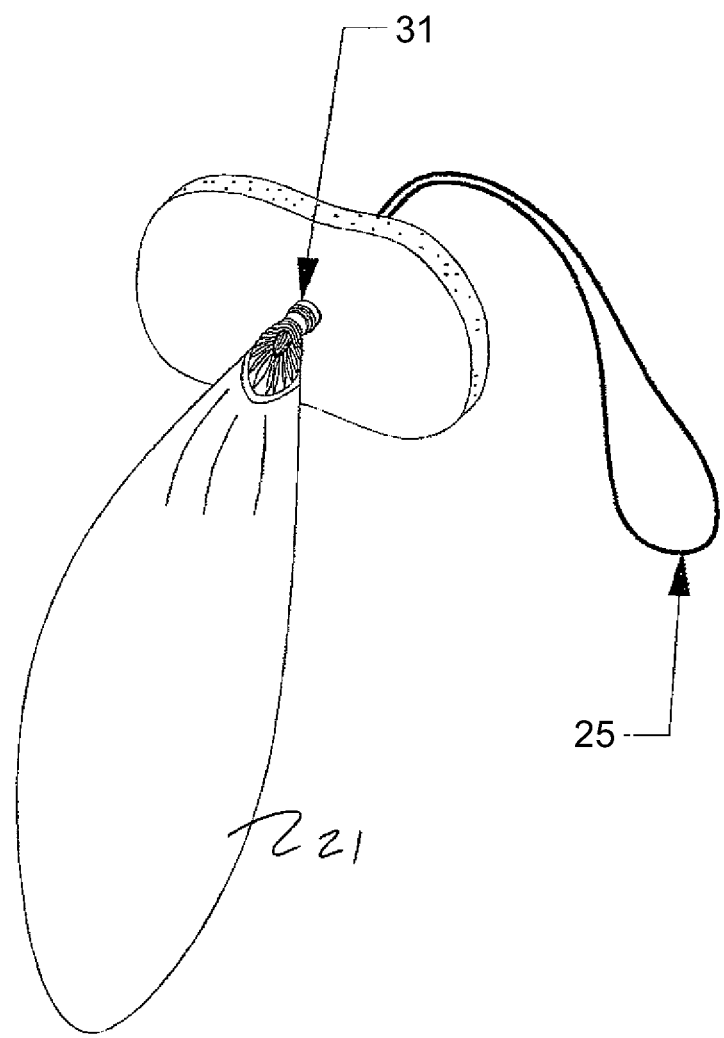
FIG. 7 is a perspective view of a specimen retrieval bag with a cord loop through a body wall in accordance with various aspects of the present invention.

Referring now to FIG. 5, at this stage, the specimen bag 21 can be completely detached and removed from the actuation rod 7 and introducer 3 by lifting the cord loop 25 from a retaining slot 7a on the actuation rod 7. In one aspect, the cord loop is a cord forming or formed into a continuous closed loop. The movable actuator or actuation rod 7 in one aspect has a retaining slot 7a located adjacent to the proximal end of the movable actuator and is arranged to frictionally hold the cord loop 25. In FIG. 6, the tissue retrieval device is withdrawn leaving behind the specimen bag 21 with the cord 25 extending through the trocar 8. As shown in FIG. 7, to protect the trocar seal and the integrity of the bag and its contents, the trocar 8 can also be withdrawn from the body wall 4 leaving the specimen bag in the body cavity and the cord loop 25 disposed across the body wall. The specimen bag 21 can be completely withdrawn from the body cavity. In some cases, a portion of the bag, for example, the neck of the specimen bag is withdrawn through the body wall. Once the neck of the specimen bag has traversed the body wall, the specimen bag is then reopened. The reopened specimen bag can then be accessed to remove or compact its contents to aid with complete withdrawal from the body cavity using an open or endoscopic instrumentation such as forceps, graspers, and aspiration probes. With the bulk of the contents removed or reduced, the specimen bag is re-closed. The cord loop 25 is pulled in a proximal direction to completely withdraw the specimen bag 21 from the body cavity. In one aspect, the bead 31 facilitates the re-opening, re-closing and/or withdrawal of the bag or portion thereof from the body cavity.

In some cases, withdrawal of the specimen bag 21 from within the body cavity can be used for small tissue specimens placed in the specimen bag, which are not likely aspirated, compacted, or removed from the specimen bag 21 prior to withdrawal of the specimen bag through the body wall. In this case, the cord loop 25 can be left attached to the actuation rod 7 and the tissue retrieval device along with the trocar can be simultaneously withdrawn from the body cavity and through the body wall.

Figure 8:
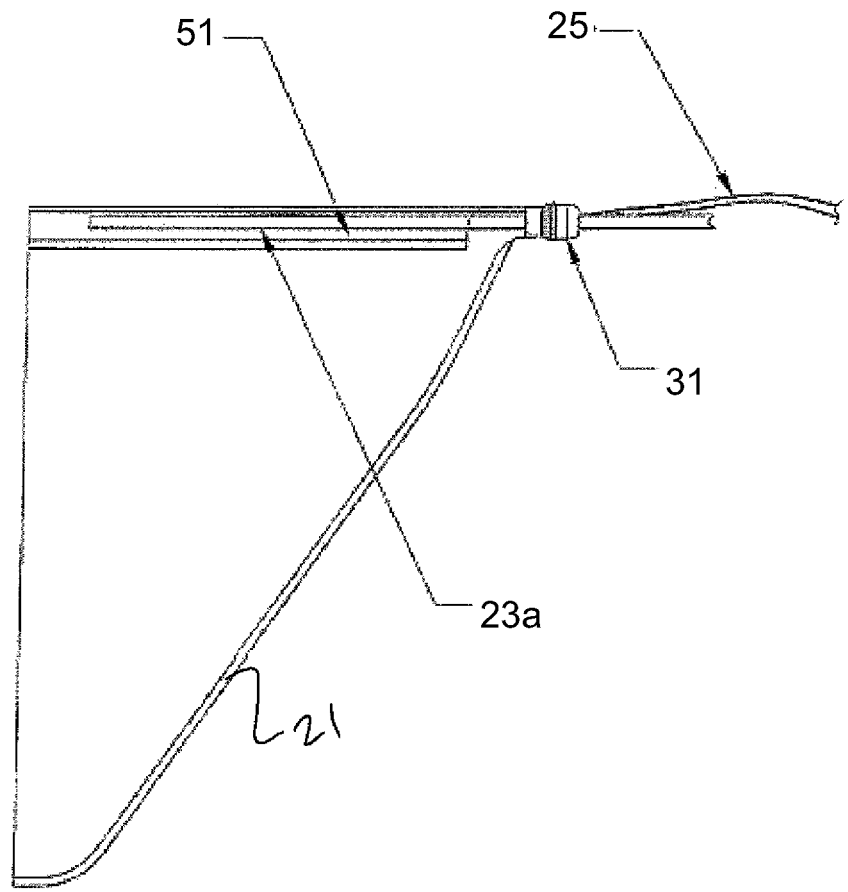
FIG. 8 is a side view of a specimen bag in accordance with various aspects of the present invention.

In FIG. 8, one aspect of a specimen bag is shown with the introducer 3 and actuation rod 7 hidden for easier visibility of the specimen bag and associated components. The specimen bag 21 has an open end 21a and a closed end 21b. Tissue collected is deposited through the open end and into the closed end of the specimen bag. The open end has a cuff that outlines all or a portion of the perimeter or periphery of the open end. The cuff defines a channel or channels arranged to receive the support arms 23a,b. In one aspect, a continuous channel is provided extending along the edge of the open end of the specimen bag with the cord 25 disposed in the channel and each support arm 23a,b insertable and removable therefrom. In one aspect, multiple channels are provided to releasably receive the support arms. For example, two channels are provided, each on opposing sides of the specimen bag and each channel is arranged to receive one of the support arms. As such, the channel is sized and dimensioned to slidably receive the support arms 23a,b and in particular, the channel or channels allow the support arms to easily retract out from the cuff or edge of the specimen bag as the actuation rod 7 is moved in the proximal direction. During assembly of the device or at least prior to use, the support arms are placed within the cuff of the specimen bag. The specimen bag and support arms in one aspect are lightly compressed, slightly adhered or frictionally mated together to ensure attachment of the specimen bag to the support arms 23a,b. The attachment is overcome by the support arms 23a,b being retracted into the introducer 3 as the support arms slide out of the cuff of the specimen bag.

The open end of the specimen bag is also attached to the cord loop 25. In one aspect, the cuff 51 confines the cord loop as the cord loop encompasses the perimeter of the open end of the specimen bag. The cuff 51 in one aspect also has a continuous channel included or integral with a channel arranged to receive the support arms and to hold the cord loop 25. In one aspect, a separate and/or adjacent channel to hold the cord loop 25 separately from the support arms 23a,b is provided. The cuff portion holding the cord loop may be reinforced for example by additional or stronger material than the remaining specimen bag to counteract tension or force applied to the cord loop during manipulation or closure of the bag and to avoid unintended separation of the bag from the cord loop. Likewise, the cuff portion holding the support arms may be reinforced for example by additional or stronger material than the remaining specimen bag to counteract forces applied by the support arms during manipulation of the device, to assist in opening the bag, to strengthen the support of the bag with the weight of tissue in the bag, to facilitate placement of tissue in the bag and to avoid unintended separation of the bag from the support arms. In one aspect, interaction with the cuff and/or channel of the specimen bag with the bead 31 can also assist in closing, reopening or reclosing of the specimen bag.

Figure 9:
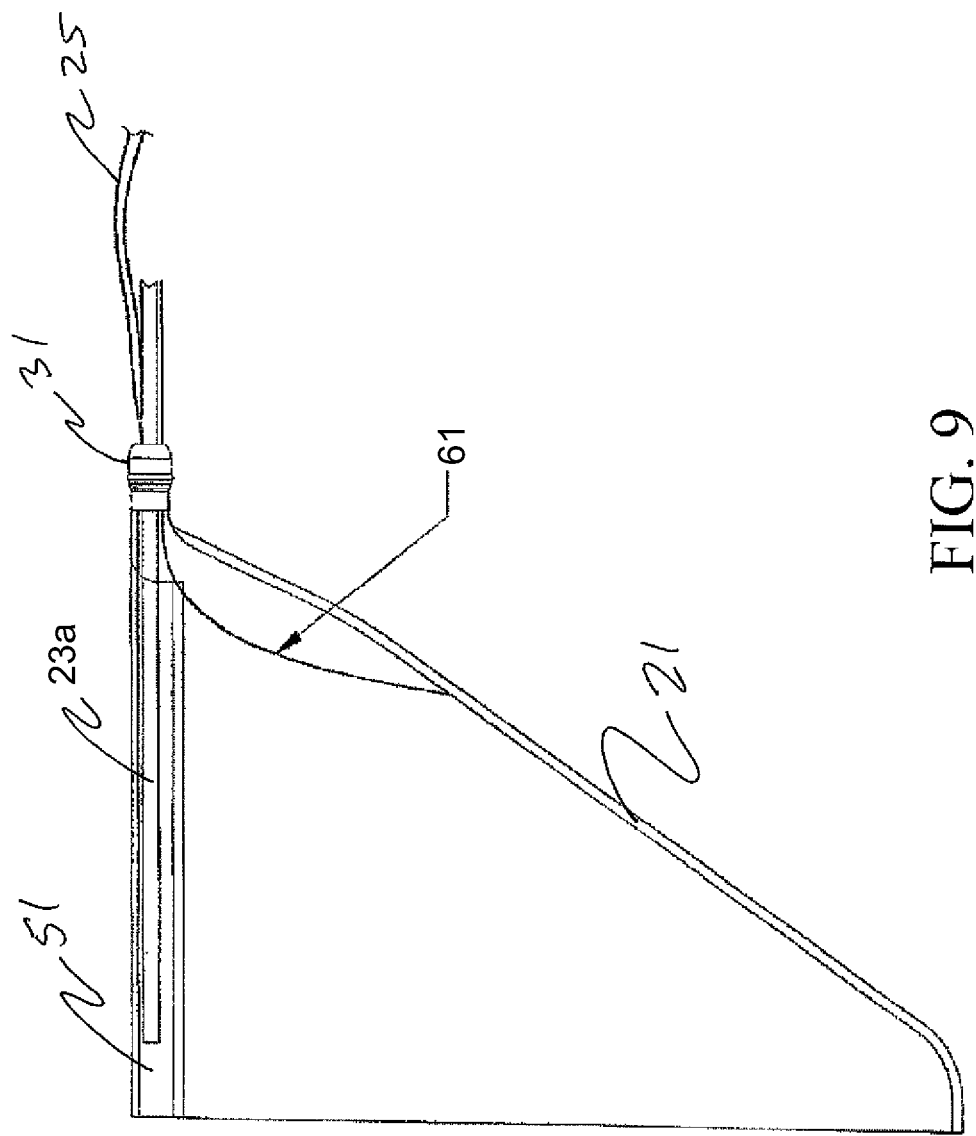
FIG. 9 is a side view of a specimen bag in accordance with various aspects of the present invention.

In one aspect, the inside surface of the specimen bag 21 is lined with a liquid absorbent material to absorb liquids such as bile to prevent inadvertent spillage of the fluid from the specimen bag. The liquid absorbent can be formed from cotton or a superabsorbant polymer. A superabsorbant polymer material is used in one aspect to initially bind the body fluid into a gel matrix to prevent spillage of the fluid during usage and manipulation within a body cavity. The gel can then be aspirated out of the specimen bag with a laparoscopic irrigation aspiration device to reduce the volume of the specimen bag prior to withdrawal from the body cavity. In one aspect, superabsorbant polymer is dispersed through the inside of the bag to spread the absorbed tissue or fluid evenly throughout the bag. In one aspect, the superabsorbant polymer is integrated into portions, placed into releasable or permeable pockets, coated or layered throughout or in select locations in the bag In FIG. 9, the tissue retrieval system in one aspect comprises a third arm 61 to enhance or facilitate the deployment of the specimen bag 21. The third arm 61 in one aspect is a spring arm positioned between or adjacent to the support arms 23a,b extending from the actuation rod 7 such that it would force the specimen bag 21 to unroll downward during deployment of the specimen bag. The third arm 61 withdraws from the specimen bag during the closing of the specimen bag and/or retraction of the support arms or movement of the actuation rod 7 in the proximal direction. As such, a first, second and third support arm, 23a,b and 61, all extend from the actuator 7 and through the guide bead 31. The third arm 61 is movable in a direction traverse to the first and second arms 23a,b. The third arm 61 in one aspect is substantially shorter than the first and second arms 23a,b.

Figure 10:
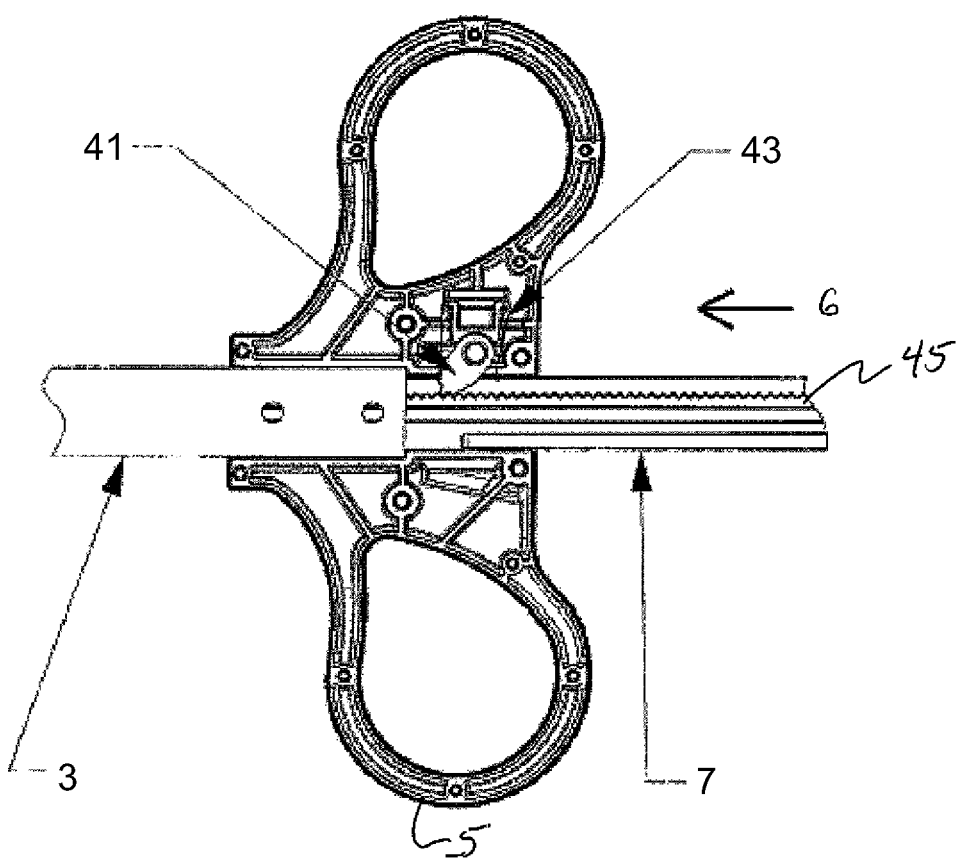
FIG. 10 is a cross-sectional side view of a portion of the tissue retrieval system with a ratchet having a pawl positioned with a specimen bag being or about to be deployed in accordance with various aspects of the present invention.
Figure 11:
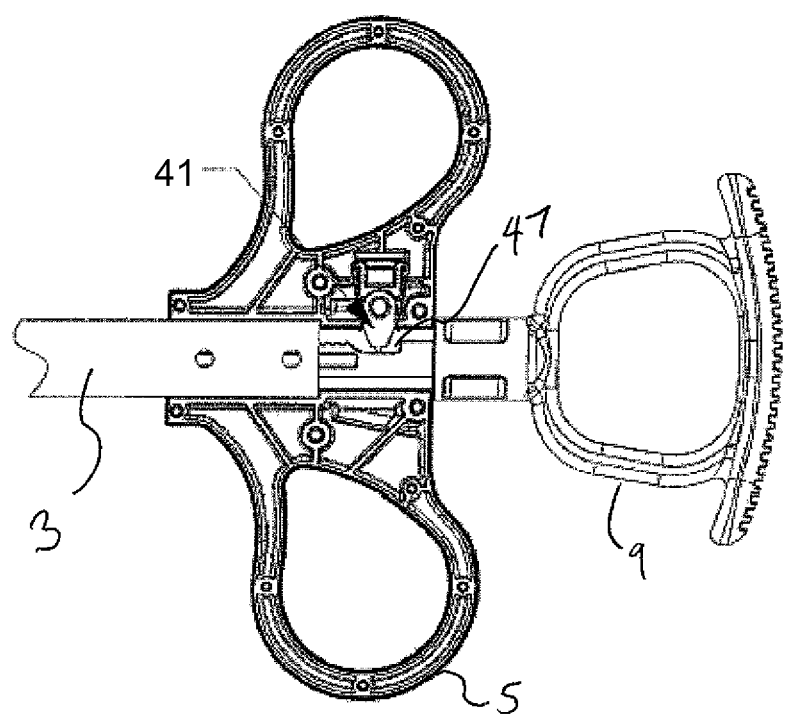
FIG. 11 is a cross-sectional side view of a portion of the tissue retrieval system with a ratchet having a pawl positioned in a neutral position after deployment of a specimen bag in accordance with various aspects of the present invention.
Figure 12:
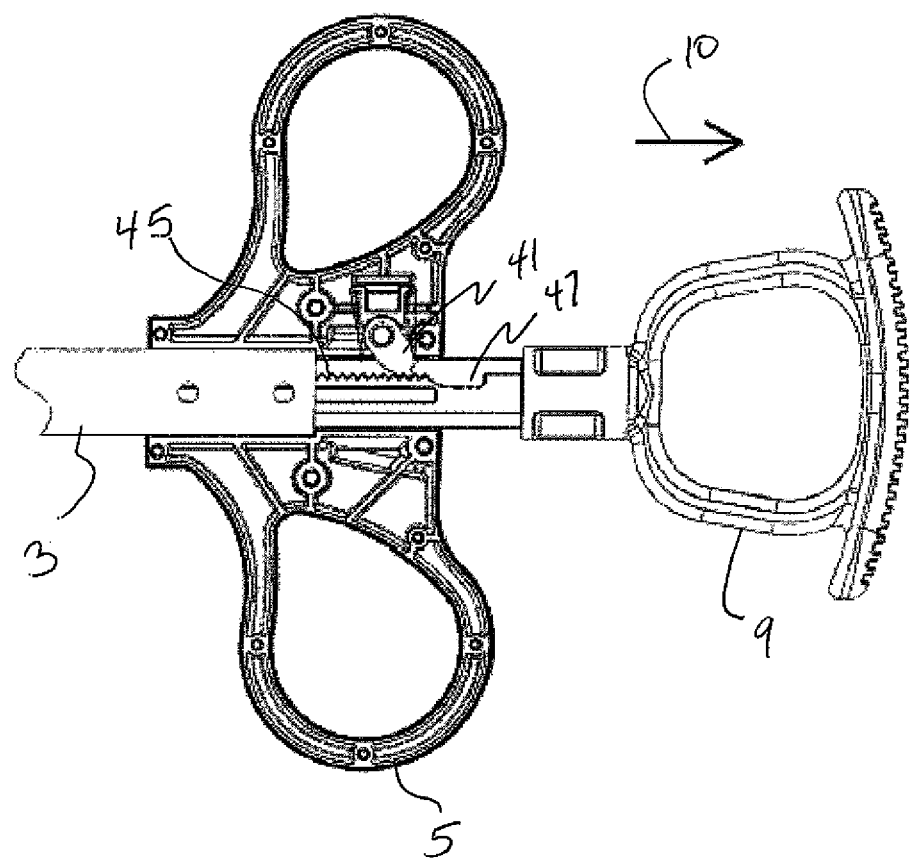
FIG. 12 is a cross-sectional side view of a portion of the tissue retrieval system with a ratchet having a pawl positioned with a specimen bag being or about to be closed in accordance with various aspects of the present invention.

Referring now to FIGS. 10-12, the actuation rod 7 and handle assembly 5 of introducer 3 in one aspect comprises a ratchet, which allows distal movement of the actuation rod 7 and prevents the actuation rod from being pulled in a proximal direction during deployment of the specimen bag. The ratchet ensures effective deployment and closure of the specimen bag. In one aspect, the ratchet comprises a pawl 41 with at least one tooth pivotally attached to a pivot pin on the handle assembly 5. The pawl operationally engages a rack 45 extending longitudinally along the actuation rod 7. In one aspect, the pawl has three teeth and a U-shaped leaf spring 43 is coupled to the pawl and biases the pawl towards a neutral position. The neutral position for the pawl 41 is the position where the central pawl tooth is generally perpendicular to the longitudinal axis of the rack 45.

The rack 45, in one aspect, has a plurality of teeth and is integral to or otherwise attached to the actuation rod 7. The pawl 41 and leaf spring 43 are nested in the handle 5 of the introducer tube 3. As such, in one aspect, the pawl 41 is pivotally connected to the handle assembly 5 of the introducer 3 and the actuation rod 7 is connected to the introducer and movable through the introducer 3. During assembly of the tissue retrieval device, the pawl 41 is initially positioned such that it is rotated clockwise from the neutral six o'clock position (FIG. 10). As such, if one tries to move the actuation rod 7 in a proximal direction, the teeth on the pawl rotate counterclockwise and bind into the teeth on the rack of the actuation rod to prevent proximal movement of the actuation rod 7. When the actuation rod 7 is moved in the distal direction, as shown by arrow 6, the pawl teeth do not bind against the rack teeth and therefore the actuation rod is free to move in the distal direction. As such, the ratchet in one aspect comprises a pawl 41 having a tooth and a rack 45 having a plurality of teeth operationally engaging with the tooth of the pawl 41. The rack 45 is attached to the actuation rod 7. In one aspect, the ratchet provides or comprises means for regulating movement of the actuator or actuation rod 7.

Operationally, the actuation rod 7 is first pushed in the distal direction until the specimen bag 21 is fully extended and deployed outside of the distal end of the introducer 3. The ratchet prevents inadvertent movement and/or unexpected movement of the actuation rod 7 in the proximal direction, which may prematurely retract a partially deployed specimen bag. For example, if the actuation rod was moved in the proximal direction during the specimen bag deployment, the support arms 23*a,b* could be fully or partially removed from the specimen bag 21. During subsequent movement of the actuation rod in a distal direction, the support arms might not realign with cuffs on the specimen bag and could be pushed through the specimen bag or not support the specimen bag.

Upon full deployment of the specimen bag 21, the pawl 41 rides down or into a ramp 47 on the rack 45, which allows the pawl to move to the neutral position (FIG. 11). As such, the ratchet is movable to a third or neutral position. With the ratchet being in the third position, the pawl 41 is substantially perpendicular to the rack 45. After the specimen is collected in the specimen bag 21, the actuation rod 7 is moved in the proximal direction, as shown by arrow 10. The pawl 41 rides up the ramp 47 on the rack 45 causing the pawl to be positioned such that it is rotated counter-clockwise from the neutral position (FIG. 12). If the actuation rod 7 is moved in a distal direction, the teeth on the pawl 41 rotate clockwise and bind into the teeth on the rack 45 to prevent distal movement of the actuation rod 7. When the actuation rod is moved in a proximal direction, the pawl teeth do not bind against the rack teeth and therefore the actuation rod is free to move in the proximal direction. The actuation rod 7 is moved proximally until in one aspect the specimen bag is fully closed and/or the support arms are fully withdrawn from the bag. In one aspect, the specimen bag is not closed until the support arms are fully withdrawn from the bag. Once the specimen bag 21 is completely closed and/or the support arms are fully withdrawn from the bag, the actuation rod in one aspect engages a stop on the handle 5 of the introducer 3 that locks or restricts further movement of the actuation rod 7 in one or both directions. As such, the stop in one aspect provides or comprises means for preventing the movable actuator from being fully withdrawn from the lumen.

The ratchet in one aspect ensures that during closure of the specimen bag 21 complete incremental closure of the bag and/or withdrawal of the support arms from the specimen bag are achieved. For example, by ensuring one way directional movement of the actuation rod 7, the support arms 23*a,b* of the actuation rod 7 may not be partially withdrawn from the specimen bag and then reinserted into the specimen bag 21. If, for example, the support arms are withdrawn and reinserted but are not aligned with the cuffs of the bag, the support arms 23*a,b* may be pushed through the specimen bag or not properly support the specimen bag. The ratchet 40 also prevents reinsertion of the support arms 23 into the body cavity after the specimen bag 21 has been detached from the device. Reinsertion of the support arms 23*a,b* into the body could decrease visibility within the body cavity and the support arms 23*a,b* could become entangled with the cord loop 25 or could become entangled with another device in the body cavity. The ratchet 40 also allows that if the tissue specimens are not voluminous, the cord loop 25 of the specimen bag 21 can be left attached to the actuation rod 7 and the tissue retrieval device along with the trocar seal and cannula can be withdrawn from the body cavity and through the body wall. The ratchet ensures that tension is maintained on the cord loop 25 and prevents the actuation rod from being pulled back into the introducer 3 as the device is withdrawn from the body cavity and through the body wall. If the introducer tube 3 alone is manually grasped during withdrawal of the device from the body cavity, an axial tensile force is naturally applied to the bead, the specimen bag, and the actuation rod by the body wall. The ratchet counteracts this tensile force to prevent movement of the actuation rod, bead, and specimen bag in the distal direction relative to the distal tip of the introducer tube.

The tissue retrieval device in one aspect has a loop of cord 25 attached to the specimen bag 21 and is held in place by or in a retaining slot 7*a* on the actuation rod 7. Once the tissue specimen is collected in the specimen bag 21 and the specimen bag closed by moving the actuation rod in the proximal direction, the cord loop 25 and retaining slot 7*a* is exposed on the actuation rod 7. To release the loop from the retaining slot, the cord loop can be grasped and pulled from the slot. The specimen bag 21 with the cord loop 25 is detached from the support arms 23 of the actuation rod 7. As such, the tissue retrieval device and the trocar cannula and/or seal can be moved in a proximal direction leaving the cord loop 25 behind, e.g., partially disposed through the body wall and partially external to the body cavity. The cord loop 25 may be withdrawn separately along with the specimen bag 21 and its contents from the body cavity and through the body wall. The cord 25 in one aspect comprises braided monofilament nylon fibers with a braided diameter of 0.025" and tensile strength of 30 lbs. The cord loop 25 enables the surgeon to easily and quickly use the cord to effect withdrawal of the specimen bag 21. The cord loop 25 also allows an application of significant axial tensile force to the cord while maintaining retention of the cord, e.g., allowing the user's finger to hook onto the cord loop 25. For example, a single strand of cord could be attached to the specimen bag. However, securing and retaining hold of a single strand of cord by hand can be difficult. In some instances, a user may use a grasping instrument to withdraw the cord but that can compromise the integrity of the cord.

In one aspect, the cord loop 25 also enables a large tensile force, if desired, to be applied to the specimen bag 21 during withdrawal of the specimen bag from a body cavity and through a body wall. During withdrawal of the specimen bag 21, a tensile force is applied by the hand of the surgeon at the proximal end of the loop 25. This tensile force is equally divided into the two strands of the loop 25 such that only half of the tensile force is applied to each strand of the cord loop. For example, if a 20-pound tensile force is applied by the surgeon to the cord loop 25 in an effort to withdraw the specimen bag 21 from a body cavity, the tensile force in each strand of the cord loop is 10 pounds. In comparison, using only a single strand cord attached to the specimen bag, when, for example, a 20 pound tensile force is applied by a user to a single strand cord, the tensile force in the strand cord is 20 pounds. The cord loop 25 as compared to a single strand cord reduces the likelihood that the specimen bag 21 can separate from the cord loop during for example withdrawal of the specimen bag from the body cavity. As such, the cord loop 25 provides an increased strength for withdrawal of a specimen bag from a body cavity.

The cord loop in one aspect can be quickly and easily released from the actuation rod 7 to detach the specimen bag 21 from the tissue retrieval device. The cord loop 25 is nested into a retaining slot 7*a* towards the proximal end of the actuation rod. The retaining slot is sized such that it is smaller than the diameter of the cord. The retaining slot 7*a* in one aspect has a relief area that allows the cord to slide while a slot interference serves to retain the cord and prevent the cord from slipping out of the slot. In one aspect, the slot interference is disposed in the actuation rod 7 generally perpendicular to the longitudinal axis of the actuation rod. In one aspect, two parallel walls in the actuation rod 7 extending perpendicular to the longitudinal axis of the actuation rod define the slot interference. A projection or detent extends in the longitudinal direction of the actuation rod 7 or generally traverse to the parallel walls from the distal parallel wall. The detent holds or catches the cord loop 25 securing or capturing the loop within the retaining slot 7a.

In one aspect, the cord 25 is not accessible until the actuation rod 7 is sufficiently withdrawn from the introducer 3 and/or the support arms 23a,b are removed from the bag 21. This prevents the bag 21 from being potentially damaged by the support arms if the bag is closed with the support arms in the bag. A portion of the cord loop is wound, looped or coiled within the introducer 3 to take up the travel distance of the actuation rod 7 relative to the introducer 3 to thereby only allow the desired timing to expose the cord for accessing by a user. A relief slot, in one aspect, is disposed near the distal end of the rod extending through the rod and having a generally rectangular shape. The excess cord is disposed through the slot and into a longitudinally extending travel slot on an opposing side of the rod opposite the side along which the cord lies on the rod from the bag to the holding slot 7a. These slots assist in preventing binding of the excess cord on the rod 7 or introducer 3 as the rod 7 is moved. As such, in one aspect, an excess length of the continuous closed loop cord 25 is looped in between the movable actuator or actuation rod 7 and the introducer tube 3. In one aspect, the cord lies or sits in a longitudinally extending travel slot along the rod 7 extending from near the distal end of the rod 7 to the retaining slot 7a. The travel slot also assists in preventing binding of the cord on the rod 7 or introducer 3 as the rod 7 is moved.

To release the cord 25 from the actuation rod 7, the cord is taken out of the slot 7a of the actuation rod 7. The tissue retrieval device can be removed from within the body cavity and through the body wall leaving the specimen bag 21 in the body cavity and the cord loop 25 disposed across the body wall. As such, cumbersome and expensive cutting elements included with the device or separately provided in which the surgeon cuts the cord in order to release the specimen bag from the device can be avoided. Also, other cumbersome and time consuming activities performed by the surgeon such as pulling on a small single strand cord to untie a slip knot to release the specimen bag from the device can further be avoided.

The cord loop 25 during manufacture of the tissue retrieval system can be easily attached to the retaining or holding slot 7a by sliding the cord loop through the holding slot, thereby cumbersome and time consuming manufacturing procedures are avoided. For example, a slip knot to secure a single strand cord to an actuation rod would cause production personnel to laboriously tie a knot at the proximal end of the cord during assembly of the device resulting in among other things an increased assembly cost for the system. In another example, a cord threaded through a pull ring with a retention knot would cause production personnel to laboriously tie a knot at the proximal end of the cord during assembly of the device resulting in an increased assembly cost for the system. In one aspect, the cord loop 25 is ultrasonically welded, bonded or mechanically crimped together and thus the cord forms a continuous closed loop.

Figure 13:
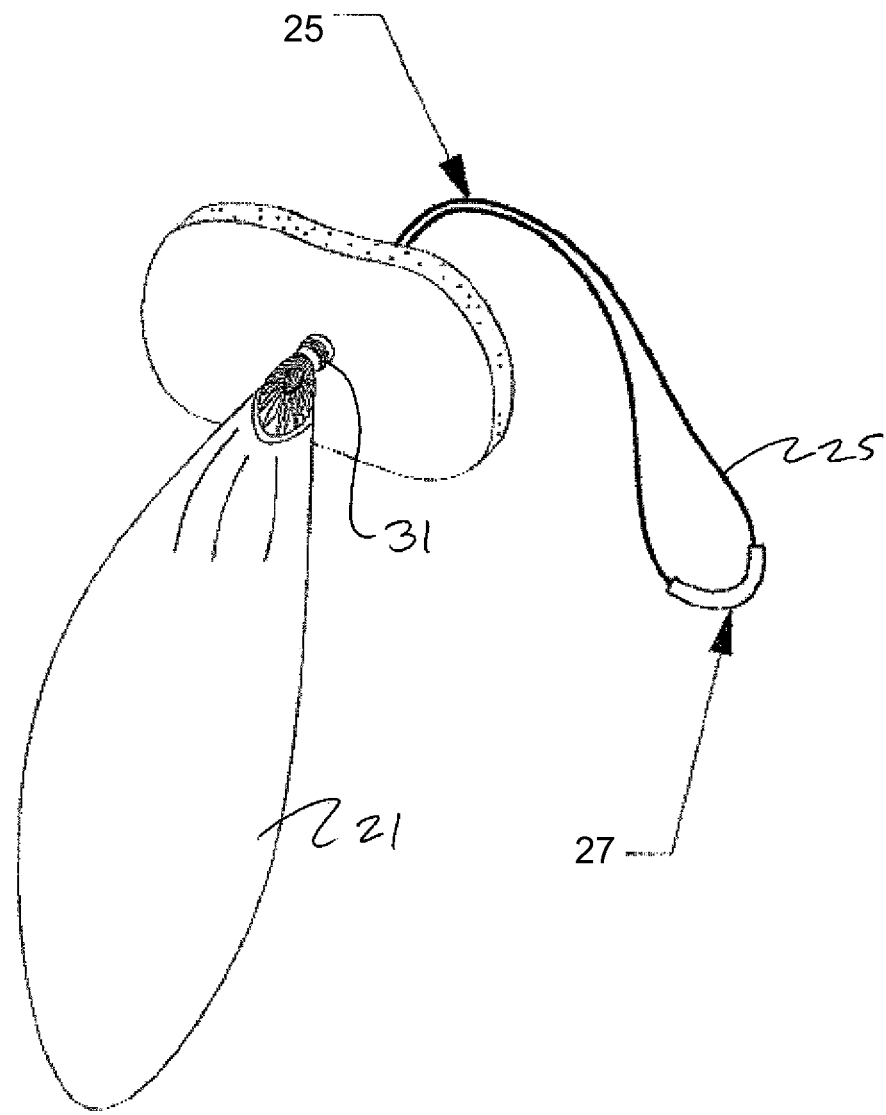
FIG. 13 is a perspective view of a specimen retrieval bag with a cord loop through a body wall in accordance with various aspects of the present invention.
Figure 14:
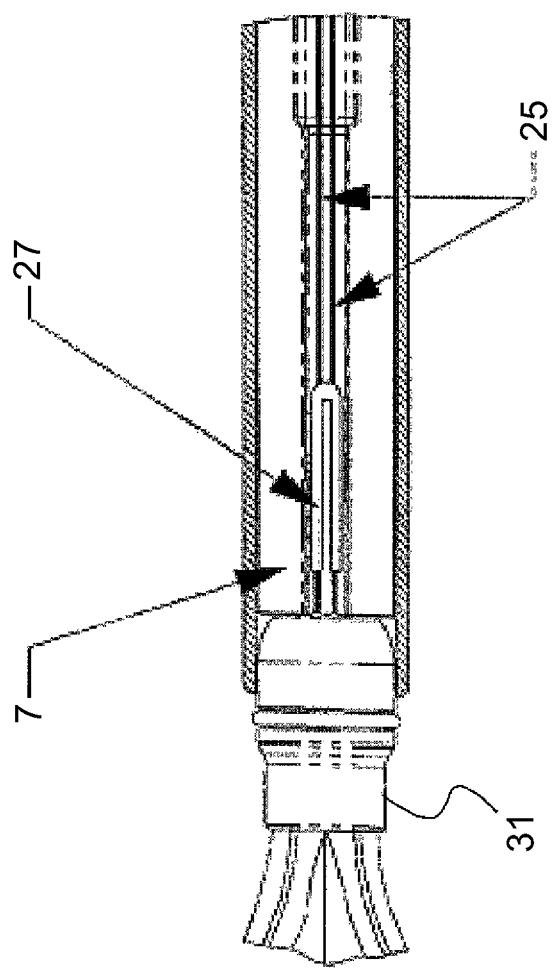
FIG. 14 is a cross-sectional top view of a distal portion of the tissue retrieval system in accordance with various aspects of the present invention.

Referring now to FIGS. 13-14, in one aspect, the cord loop 25 comprises a handle 27 or gripping member attached to the cord loop to aid with withdrawal of the specimen bag. The gripping member can be formed from an elastomeric tube such that the cord is threaded through the tube. The gripping member or handle can also be positioned towards the distal tip of the actuation rod 7 such that the cord 25 slides through the introducer to enable cinching of the specimen bag. Upon detachment of the cord loop 25 from the actuation rod 7, the cord slides through the introducer until the proximal end of the cord loop 25 pulls the introducer from the actuation rod thereby exposing the gripping handle on the proximal end of the cord loop. As such, a gripping member or handle 27 is connected to the cord loop 25 and is movable within the lumen of the introducer tube 3. The gripping handle 27 in one aspect is substantially tubular with a lumen having a diameter corresponding to a diameter of the cord.

Figure 15:
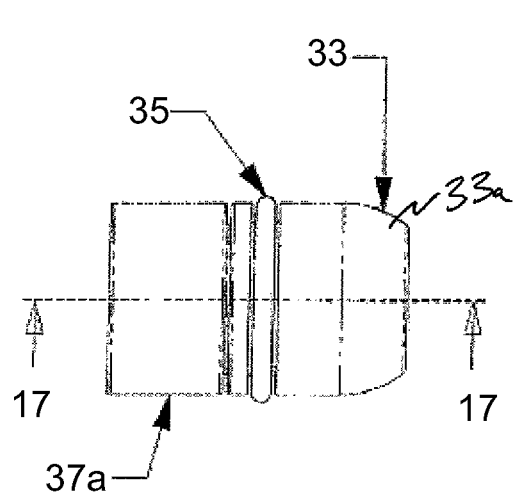
FIG. 15 is a side view of a bead in accordance with various aspects of the present invention.
Figure 16:
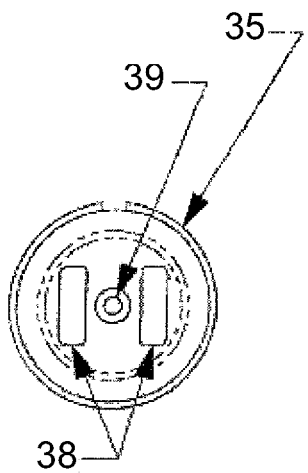
FIG. 16 is a cross-sectional front view of a bead in accordance with various aspects of the present invention.
Figure 17:
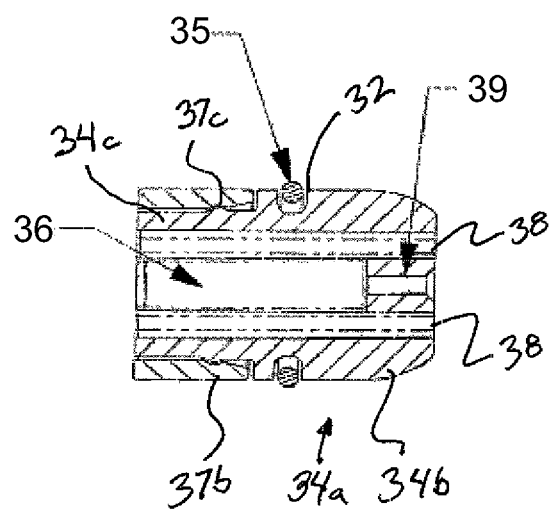
FIG. 17 is a cross-sectional side view of a bead in accordance with various aspects of the present invention.

Referring now to FIGS. 15-17, the tissue retrieval device, in one aspect, comprises a bead 31 coupled to the cord loop 25. The guide bead in one aspect is substantially cylindrical. The bead has a hole or bore 39 centered along its longitudinal axis through which the cord loop 25 traverses. The hole 39 is sized such that the bore frictionally engages the cord 25 to retain the specimen bag 21 in a closed configuration once the specimen bag 21 has been closed. At least one support arm extends from the actuator and through the guide bead. The guide bead in one aspect has at least one slot 38 is adjacent to the bore 39 through which the at least one support arm extends through. As such, the at least one support arm 23a or 23b extends from the actuator and through the guide bead 31. When the specimen bag 21 is detached from the device leaving the specimen bag 21 in the body cavity with the cord loop 25 disposed through the body wall, the cord loop 25 can be withdrawn until the bead 31 and a partial portion of the specimen bag, e.g., the cuff portion of the specimen bag, are exterior to the body wall while the collected specimen is still positioned in the body cavity.

The specimen bag 21 can be reopened by moving the distal end of the specimen bag rim and the bead 31 in opposite directions of each other. The contents of the specimen bag 21 can be accessed while the specimen bag lines and protects the body wall from contamination. For example, the specimen bag 21 can be accessed with an aspiration device to remove collected fluids such as bile from the gallbladder to reduce the volume of the specimen bag contents. By reducing the volume of the contents of the specimen bag, the specimen bag can be completely withdrawn through the body wall without enlarging the opening in the body wall.

In another example, if the contents of the specimen bag 21 include a large number of gallstones, the gallstones can be accessed with a laparoscopic grasper or forceps and removed one by one to reduce the volume of the specimen bag contents to facilitate withdrawal of the remainder of the specimen bag 21 through the body wall. Likewise, the specimen bag 21 can be reopened to place additional gallstones with a laparoscopic grasper or forceps and then reclosed with the grasper or with the assistance of the grasper or by pulling the cord loop which automatically recloses the specimen bag 21 as the bead 31 enters the incision site. With all the blood, irrigation and tissue debris at the surgical site, it may be difficult to find spilled stones, so by first closing the bag and isolating the contents, irrigation and suction can be introduced to clear the site for better visibility of the material to be removed. The surgeon may have to introduce a large grasping instrument to get a secure grip on the stone and pull it through the trocar cannula 8b. However if the stone is large, the jaws of the grasper may not completely close and thereby may not fit through the trocar cannula. Forcing the jaws closed may push the stone out of the jaws or crush it into particulate potentially dropping infected contents back into the abdomen.

The specimen bag 21 can also be closed prior to its complete withdrawal from the body cavity by pulling the bead 31 and the cord loop 25 in opposite directions until the specimen bag 21 is cinched closed. Likewise by reversing the operation, the specimen bag can be reopened. As such, the guide bead 31 is movable from a first position to close the tissue bag 21 to a second position to open the tissue bag 21. By allowing the bag 21 to be closed and reopened as desired through interaction of the bead 31 and the cord loop 25, multiple time consuming, cumbersome and potentially undesirable operations are reduced or eliminated. For example, a knot or a noose on the cord utilized to retain a specimen bag in a closed configuration does not allow the specimen bag to be easily reopened and a surgeon will typically cut off the rim portion of the specimen bag to gain access to the contents of the specimen bag prior to withdrawal from the body cavity. As the rim is cut off, the cord is also removed. The surgeon then attaches clamps around the opening of the specimen bag to secure the specimen bag and to prevent it from retracting back into the body cavity. With the cord and rim of the specimen bag removed, the clamp is used to close the bag after additional tissue is added and subsequently withdraw the specimen bag out of the body cavity. If the bag is to be reopened again, it becomes difficult to reposition the clamp to both secure and open the bag and also to close and withdraw the bag out of the body cavity. Also, with the rim of the bag removed, the volume available in the bag to accommodate tissue and the area available to grasp and manipulate the bag are substantially reduced.

The bead 31, being generally cylindrical for example, in one aspect also serves to facilitate withdrawal of the specimen bag 21 through the body wall by acting as a dilator and guide. If a dilating or separating trocar, for example, is first used to traverse a body wall such as the abdominal wall to create an access site for insertion of a tissue retrieval system, the opening in the body wall can be minimal in size, making withdrawal of a specimen bag 21 difficult. When the specimen bag 21 is detached from the device with the cord loop 25 left disposed through the body wall, as the cord loop 25 is pulled away from the body wall, the bead 31 is pulled into the body wall and acts to dilate the opening, conduit and/or access channel and/or separate the muscle and tissue fibers of the body wall. The bead 31 in one aspect is shaped such that a dilating tip 33 or the leading portion (relative to moving out of the body) includes a blunt and tapered end 33a to enable the separation of the muscle and tissue fibers. In one aspect, the guide bead is substantially cylindrical having a sloped proximal end. As the bead 31 traverses the body wall, the cinched rim of the bag 21 and the remainder of the bag can easily follow with the bead 31 leading the way and the cinched rim of the bag 21 gathered in-line behind the bead 31. Thus, the bead 31 avoids the reliance on the bunched and closed rim of the specimen bag 21 to force its way through the body wall during withdrawal of the specimen bag 21. Without the bead 31 leading the way, the bunched rim of tissue bag and/or the cord may catch on the body during withdrawal of the specimen bag through the body wall.

The bead 31 also in one aspect is configured to prevent the specimen bag 21 from being pulled into the central bore 39 in the bead 31, which frictionally engages the cord loop 25. For example, in one aspect, the depth of the cord engagement bore 39 or central bore of the bead 31 through which the cord loop 25 runs extends from the proximal end of the bead 31 for approximately 0.125" while the overall length of the bead is approximately 0.530". The distal portion of the bead is hollowed out to provide space, a hollow space 36, allowing the specimen bag 21 to be partially pulled into during cinching of the specimen bag 21. The central bore 39 on the bead 31 which frictionally engages the cord loop 25 is approximately 0.035" in diameter and is positioned a sufficient axial distance from the distal end of the bead such that when the specimen bag 21 is cinched closed, the specimen bag 21 is not pulled into the central bore 39 in the bead 31. This spacing between the central bore 39 and the distal end of the bead 31 prevents the specimen bag 21 from being pulled into the bore and becoming wedged between the cord loop 25 and the central bore 39. If the specimen bag 21 is allowed to be pulled into the central bore 39 of the bead 31 during closure of the specimen bag 21, the specimen bag 21 could become wedged between the central bore 39 and the cord loop 25 and could prevent further movement of the cord loop 25 and thus closure of the specimen bag 21. In one aspect, the introducer 3 has a longitudinally extending lumen with a first diameter and the actuator 7 is movable through the lumen. The guide bead 31 has a second diameter substantially equal to the first diameter of the introducer 3.

The bead 31 also in one aspect enables or facilitates the closure of the specimen bag 21. For example, the bead 31 in one aspect has a radial groove 32 in which a retaining ring 35 is disposed. The retaining ring 35 as such in one aspect encircles a portion of the guide bead 31. The retaining ring 35 in one aspect is made of tempered stainless steel with a circular cross-section. The retaining ring 35 is configured such that it can expand and compress. In one aspect, the retaining ring 35 is "C-shaped" or has a radial gap cut through the ring to facilitate expansion and compression of the ring 35. The retaining ring 35 is positioned onto the bead 31 such that the retaining ring does not move longitudinally along the axis of the bead and/or out of a groove 32 disposed partially or completely around the periphery of the bead.

During assembly of the device and/or prior to use, the specimen bag 21 with the affixed bead can be pre-rolled and stored in the introducer 3. In this state, the retaining ring 35 is compressed by the introducer 3 which has an inside diameter that is smaller than the non-compressed diameter of the retaining ring 35. Upon deployment of the specimen bag 21 from the introducer 3, the bead 31 and the retaining ring 35 also deploy out of the distal end of the introducer 3. Once the bead 31 with the retaining ring 35 is deployed out of the introducer 3, the retaining ring 35 expands, e.g., to its original or approximately pre-compressed diameter. The retaining ring 35 prevents the bead 31 from being entirely pulled or withdrawn proximally into the introducer 3. For example, as the specimen bag 21 is closed via application of an axial tensile force on the cord loop 25, the retaining ring 35 limits the bead 31 from sliding or otherwise being withdrawn into the introducer 3 and thereby prevents the specimen bag rim or cuff from also being pulled into the introducer 3. The introducer tube 3 in one aspect has a longitudinally extending lumen with an inner diameter that generally corresponds or is substantially equal to the outer diameter of the guide bead and thereby with the retaining ring 35 is limited from moving back into the introducer 3. As such, the guide bead 31 in one aspect provides a means for frictionally engaging the cord loop and in one aspect is arranged to move out of the lumen of the introducer and restricted from moving back into introducer.

As shown in FIG. 17, the bead 31 in one aspect comprises of two components 34a, 37a to couple the bead 31 to the specimen bag 21. The first bead component 34a comprises a dilating portion 34b at its proximal end and a cylindrical tubular portion 34c at its distal end. The second bead component 37a comprises a capture ring designed to slide over the cylindrical portion 34c of the first bead component 34a. The second bead component or capture ring 37a has an annular snap fit 37c to engage and lock onto the cylindrical portion 34c of the first bead component 34a. The specimen bag 21 in one aspect has a tubular portion or an extended cuff channel to slide over the cylindrical portion 34c of the first bead component 34a. The second bead component 37a positioned over the tubular portion of the specimen bag captures the specimen bag 21 between the two bead components 34a, 37a thus coupling the bead 31 to the specimen bag 21. As such, in one aspect, the capture ring 37a encompasses a portion of the guide bead 31 and a portion of the tissue bag 21 such that a portion of the tissue bag is positioned and thereby captured or secured between the capture ring 37a and the guide bead 31. Alternatively, the bead 31 in one aspect could be a single component and the specimen bag bonded with an adhesive to a portion of the bead 31, e.g., an exterior surface of the cylindrical portion 34c of the bead 31.

The tissue retrieval device or system in one aspect comprises multiple components. The introducer 3 is an extruded ABS (Acrylonitrile Butadiene Styrene) tube that has machined holes at its proximal end that engage positioning pins on the upper handle and the lower handle to prevent axial and rotational movement of the tube relative to the handle 5. The upper handle and the lower handle, that form handle 5, are injection molded with polycarbonate. The introducer 3 in one aspect is injection molded as a single component and in one aspect as two components. The actuation rod 7 in one aspect comprises five components; an injection molded polycarbonate actuation rod, a molded EPDM (Ethylene Propylene Diene Monomer) rubber O-ring, an injection molded polycarbonate support cover, and two stamped 17-7 stainless steel support arms 23a,b. An O-ring fits into a receiving groove on the actuation rod 7 and serves to prevent loss of pneumoperitoneum through the system by sealing on the inside diameter of the introducer 3.

The support arms 23a,b fit into recesses in the distal end of the actuation rod 7 and is trapped in place by the support cover, which snaps in place on the actuation rod 7. In various aspects a single support arm is provided extending from the actuator 7 to support the bag 21. In various aspects, a plurality of support arms is provided extending from the actuator 7 to support the bag 21. The specimen bag 21 in one aspect is produced from a 0.004" thick polyurethane film. A die cut pattern is produced from the film. Welding is conducted to create the cuff portion 51 of the specimen bag 21. The cuff is formed by folding over the top edge of the die cut pattern and an impulse type heat sealer is used to create the cuff seam. Welding is conducted to form the final or desired shape of the bag 21. The film with the formed cuff is folded in half along its longitudinal axis such that the cuff is on the inside of the folded halves. An impulse type heat sealer is used to weld and cut the specimen bag to produce the final or desired configuration. The specimen bag sub-assembly in one aspect comprises five components; a specimen bag, a braided nylon cord loop, an injection molded polycarbonate bead, an injection molded capture ring, and a formed 302 stainless steel retaining ring. The cord 25 is fed through the cuff 51 on the specimen bag 21 and tied into a loop using a modified overhand knot. The knot is positioned such that it is located towards the distal end of the specimen bag rim. The capture ring 37a is positioned over the cord loop 25 and over the tubular portion of the specimen bag. The retaining ring 35 is pressed into position in a groove on the bead. The cord loop 25 is fed through the central bore 39 on the bead 31. The tubular portion of the specimen bag 21 is fed over the distal portion of the bead and the capture ring 37a snap fitted over the tubular portion of the specimen bag 21 to attach the bead 31 to the specimen bag 21.

In one aspect, the O-ring is slid onto the actuation rod 7. The support arms 23a,b are fed through slots 38 on the bead 31 and into the cuffs on the specimen bag 21. The support arms 23a,b are nested into the actuation rod 7 and a support cover is press fitted into place. The cord loop 25 on the specimen bag 21 is run underneath the O-ring and slid through the holding slot on the actuation rod 7. The specimen bag 21 is tightly rolled from the bottom to the top cuff portion of the specimen bag 21. The cord loop 25 is folded and laid into a receiving channel on the actuation rod 7. The actuation rod 7 with the specimen bag 21 is pushed through the proximal end of the introducer 3 until the rolled up specimen bag is flush with the distal end 3a of the introducer 3. The upper handle is positioned on the introducer 3 and the pawl 41 and pawl spring 43 are positioned on the upper handle. The pawl 41 is positioned such that its teeth are rotated clockwise relative to its neutral six o'clock position. The lower handle is press fitted onto the upper handle to form handle 5.

Figure 18:
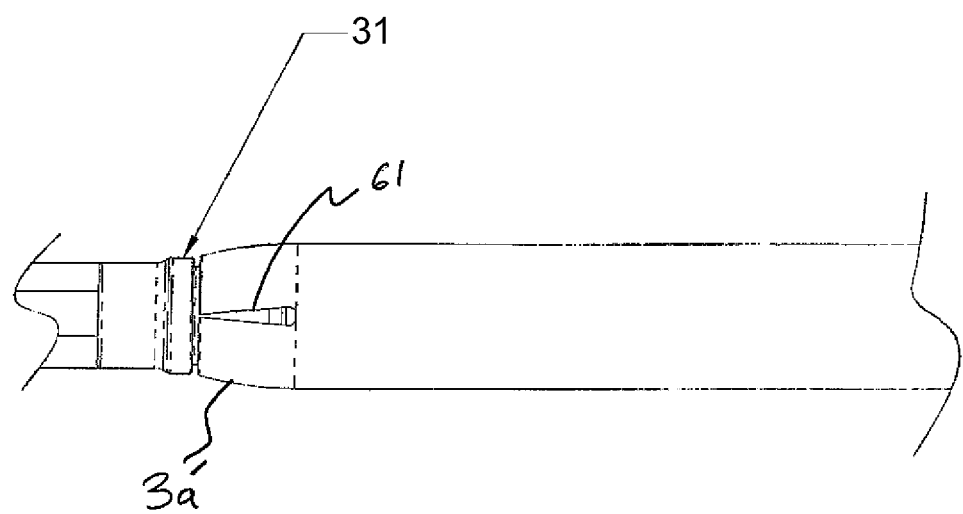
FIG. 18 is a top view of a distal portion of the tissue retrieval system in accordance with various aspects of the present invention.

In one aspect, in FIG. 18, the distal tip or end 3a of the introducer 3 is a tip 3a' formed such that the inside diameter of the tube would be smaller at its distal end 3a as compared to the diameter along the remainder of the tube. The bead 31 is sized such that upon deployment of the specimen bag, the bead 31 dislodges from within the introducer 3, and abuts the tip formed end 3a' of the introducer 3 during the closing of the specimen bag 21 to assist in closing the specimen bag 21. The distal tip 3a' of the introducer 3 in one aspect also has one or more longitudinal slots 61 to enable the tube to more readily expand as the coiled or rolled specimen bag 21 is advanced through the introducer tube.

Figure 19:
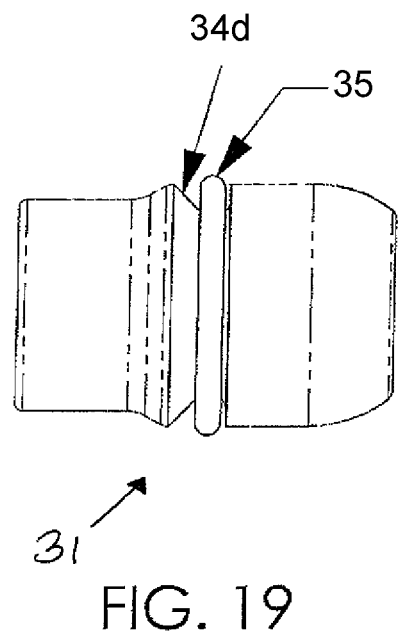
FIG. 19 is a side view of a bead in accordance with various aspects of the present invention.
Figure 20:
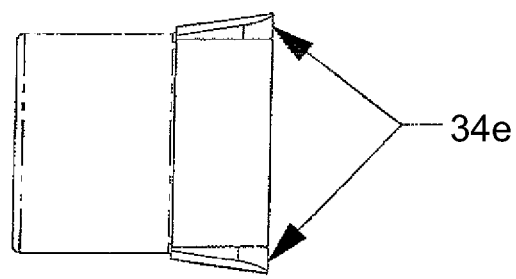
FIG. 20 is a side view of a bead in accordance with various aspects of the present invention.
Figure 21:
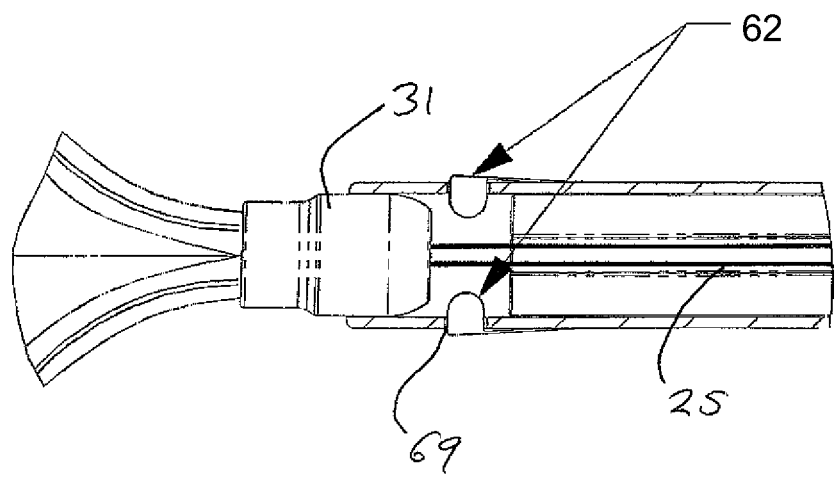
FIG. 21 is a cross-sectional top view of a distal portion of the tissue retrieval system in accordance with various aspects of the present invention.

In one aspect, the retaining ring 35 on the bead 31 is formed from an elastomeric material. In FIG. 19, in one aspect, the bead 31 has a ramped portion 34d which forces the diameter of the retaining ring 35 to expand during the cinching or closing procedure of the specimen bag 21 thereby preventing the bead 31 from being withdrawn into the introducer 3. In one aspect, as shown in FIG. 20, the bead 31 has expanding arms 34e which upon initial deployment of the specimen bag 21 would abut the distal end 3a of the introducer 3 to prevent the bead 31 from being withdrawn into the introducer 3 facilitating the closing of the specimen bag 21. In FIG. 21, in one aspect, the introducer 3 has a separate spring member 62 attached or disposed at the distal tip or end 3a and positioned and sized such that the spring member 62 or portions thereof 62a would protrude into the inside diameter of the introducer 3. In one aspect, one or more spring arms with one or more projections or protrusions of spring member 62 are engaged into receivers such as holes, cavities and/or slots 69 in the introducer 3 and resilient flex outward from the inner lumen of the introducer 3. The spring member flexes allowing the coiled or rolled specimen bag 21 and the bead 31 to pass through the introducer 3 during or prior to deployment of the specimen bag 21, but remains in place preventing the bead 31 from being withdrawn into the introducer 3 after deployment of the specimen bag 21. As such, a resilient arm or spring member 62 is connected to the introducer 3 and operationally engaging the guide bead 7. The arm is being movable in a first direction allowing movement of the guide bead 31 in a distal direction and in a second direction preventing movement of the guide bead 31 in a proximal direction back into the introducer 3.

Figure 22:
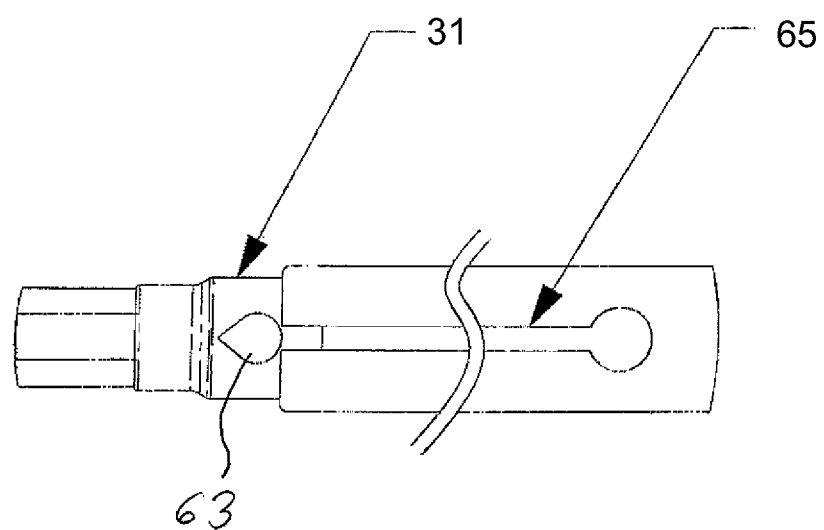
FIG. 22 is a top view of a distal portion of the tissue retrieval system in accordance with various aspects of the present invention.

Referring now to FIG. 22, in one aspect, the introducer 3 is formed with one or more longitudinal slots 65 such that the bead 31 with one or more projections or protrusions 63 could be forced through the slot during deployment of the specimen bag 21 but is prevented from being withdrawn back into the introducer 3. As such, the introducer 3 in one aspect has a slot 65 longitudinally extending along and/or through a portion of the distal end. The guide bead 31 with a projection 63 engages the slot and is arranged to allow movement of the guide bead 31 in a distal direction and prevents movement of the guide bead 31 in a proximal direction back into the introducer 3.

Figure 23:
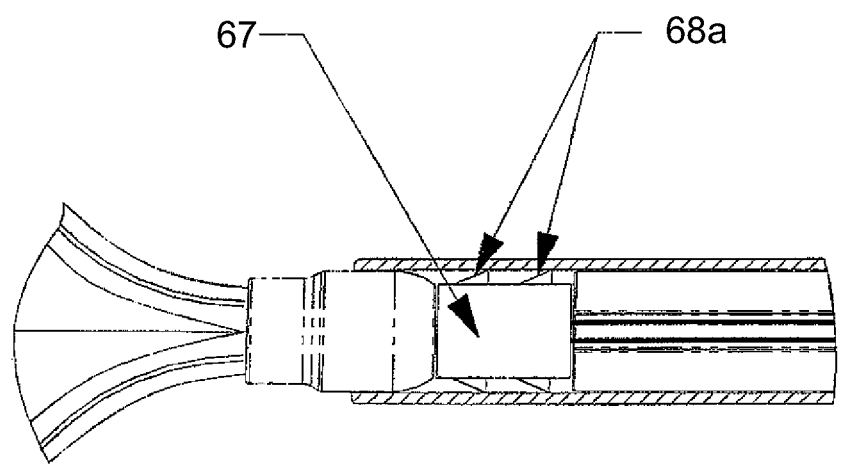
FIGS. 23-25 are cross-sectional top views of a distal portion of the tissue retrieval system in accordance with various aspects of the present invention.
Figure 24:
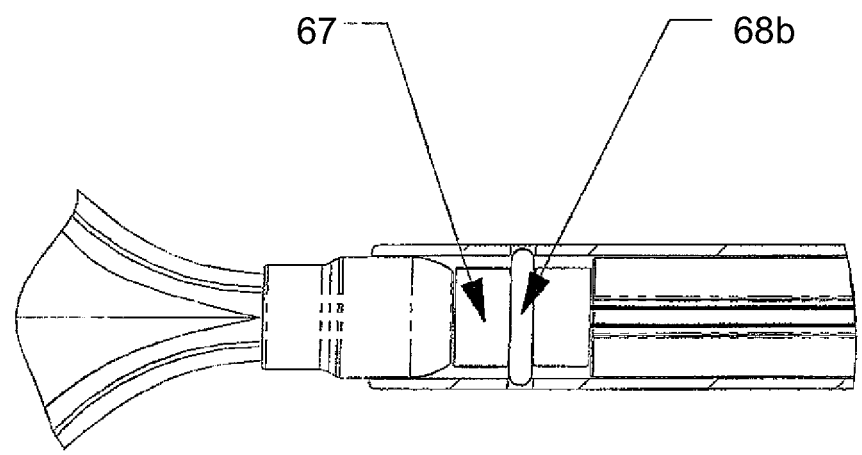
Figure 25:
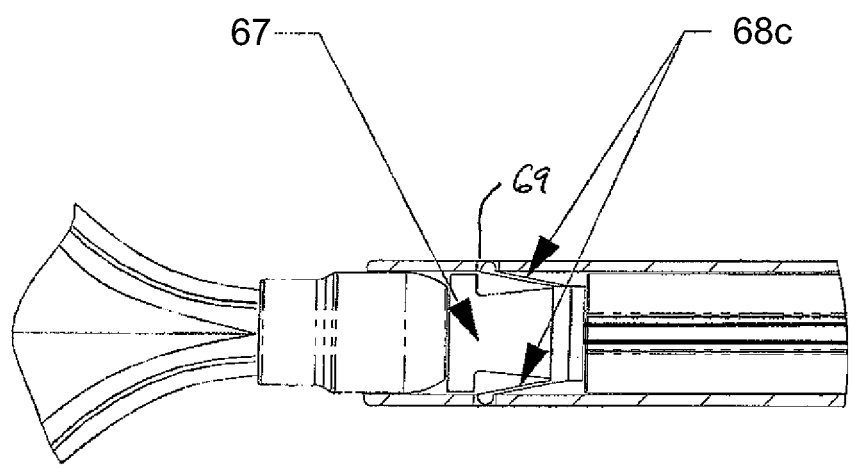

In FIGS. 23-25, in one aspect, the tissue retrieval device comprises an intermediate collar 67 that slides into a locking position at the distal tip or end 3a of the introducer 3 during and/or after deployment of the specimen bag 21. The collar 67 is positioned between the actuation rod 7 and the bead 31. Once the collar 67 is locked in position, the collar 67 prevents the bead 31 from being withdrawn back into the introducer 3. In one aspect, the collar has a projection arranged to prevent movement of the guide bead in a proximal direction. For instance, the collar 67 in one aspect has one-way barbs 68a to lock it in position. The collar 67 in one aspect has a retaining ring 68b to lock it in position. The collar 67 in one aspect has one or more spring arms 68c that would move outward or portions thereof would engage into receivers such as holes, cavities and/or slots 69 in the introducer 3 to lock it in position.

Figure 26:
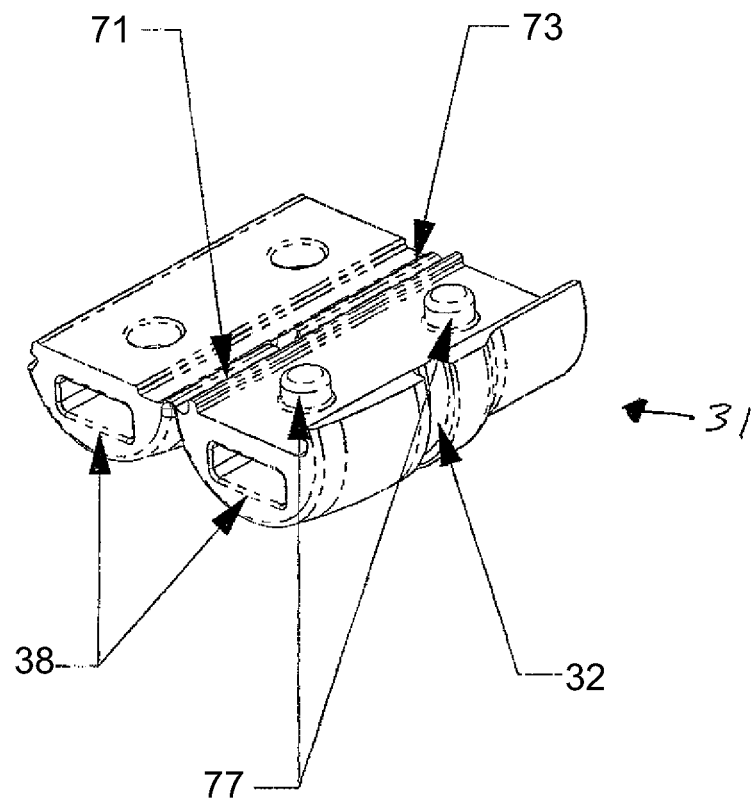
FIG. 26 is a perspective view of a bead in accordance with various aspects of the present invention.

In one aspect, the bead 31 is formed as one piece and the specimen bag 21 bonded to the bead with an adhesive. The specimen bag 21 in one aspect is attached to the bead by trapping the specimen bag between the bead and a small length of shrink tubing. In one aspect, as shown in FIG. 26, the bead 31 is molded in one piece with a living hinge 73 and then folded in half to capture the specimen bag. The bead in one aspect has capture posts 77 to capture the specimen bag 21 during folding of the bead. The bead also has a cord engagement groove 71 for securing though allowing passage there through the cord loop 25.

The specimen or tissue retrieval device or system in general provides an easy to use system that effectively contains excised tissue specimens, prevents loss or spillage of tissue specimens into a body cavity, and protects the body wall access port site from contamination with the excised tissue specimens during withdrawal of the tissue specimens from within the body cavity. The tissue retrieval system in various aspects include a ratcheting mechanism which ensures effective deployment and cinching of the specimen bag, a cord loop attached to the specimen bag which aids with withdrawal of the specimen bag through a body wall, a bead attached to the specimen bag which serves as a dilator during withdrawal of the specimen bag to separate body wall muscle and tissue fibers, and a frictional lock on the bead which enables the specimen bag to be cinched closed and then re-opened as desired.

Although the present invention has been described in certain specific aspects, many additional modifications and variations would be apparent to those skilled in the art. It is therefore to be understood that the present invention may be practiced otherwise than specifically described, including various changes in the size, shape and materials, without departing from the scope and spirit of the present invention. Thus, embodiments of the present invention should be considered in all respects as illustrative and not restrictive.

The invention claimed is:

1. A tissue retrieval apparatus comprising:
    an introducer having a longitudinally extending lumen;
    an actuator slidable within the lumen of the introducer;
    a tissue bag having an open end and a closed end, the open end of the tissue bag connected to the actuator;
    a cord attached along a periphery of the open end of the tissue bag and to the actuator; and
    a substantially cylindrical guide bead comprising a retaining ring encircling a portion of the guide bead, the retaining ring compressible to a compressed state wherein the guide bead has an initial position entirely within the longitudinally extending lumen of the introducer and the retaining ring expandable to an expanded state upon deployment from the longitudinally extending lumen wherein the retaining ring is restricted from reentering the longitudinally extending lumen of the introducer, the guide bead having a hole longitudinally extending therethrough sized to frictionally couple to the cord and the guide bead being independently movable along the cord.

2. The apparatus of claim 1, wherein the longitudinally extending lumen of the introducer has a first diameter and the guide bead has a second diameter substantially equal to the first diameter of the lumen of the introducer.

3. The apparatus of claim 1 wherein the guide bead is substantially cylindrical having a sloped proximal end.

4. The apparatus of claim 1 wherein the guide bead is made of a first material and the cord is made of a second material, the first material being different from the second material.

5. The apparatus of claim 1 wherein the guide bead is less resilient than the cord.

6. The apparatus of claim 1 wherein the guide bead is arranged to assist in withdrawal of the tissue bag from a body wall.

7. The apparatus of claim 1 wherein the guide bead is movable from a first position to close the tissue bag to a second position to open the tissue bag.

8. The apparatus of claim 1 further comprising a capture ring encompassing a portion of the guide bead and a portion of the tissue bag being positioned between the capture ring and the guide bead.

9. The apparatus of claim 8, wherein the capture ring has an annular snap fit to engage the guide bead.

10. The apparatus of claim 1 wherein the cord is a single continuous closed loop.

11. The apparatus of claim 10 further comprising a handle connected to the cord, the handle being substantially tubular with a handle lumen with a diameter corresponding to a diameter of the cord.

12. The apparatus of claim 1 further comprising at least one support arm extending from the actuator and through the guide bead.

13. The apparatus of claim 12 wherein the guide bead has a bore through which the cord extends through and at least one slot adjacent to the bore through which the at least one support arm extends through.

14. The apparatus of claim 1 further comprising a first, second and third support arm, all extending from the actuator and through the guide bead.

15. The apparatus of claim 14 wherein the first and second arms are movable in a first direction and the third arm is movable in a direction traverse to the first direction.

16. The apparatus of claim 14 wherein the third arm is substantially shorter than the first and second arms.

17. The apparatus of claim 1 wherein the tissue bag comprises a superabsorbant polymer.

18. The apparatus of claim 1 wherein the retaining ring has a radial gap cut formed therein.

19. A tissue retrieval apparatus comprising:
    an introducer tube having a longitudinally extending lumen with a handle assembly extending from one end of the introducer tube, the handle assembly having a pair of finger loops;
    an actuation rod having a proximal and a distal end and movable through the lumen, the distal end having a plurality of support arms and the proximal end having a handle;
    a tissue bag having an open end and a closed end, the open end releasably coupled to the support arms and having a continuous cord loop attached to the open end of the tissue bag and being releasably attached to the movable actuation rod, the tissue bag movable from a stored position within the lumen of the introducer tube to a deployed position;

a guide bead having a compressible retaining ring, the retaining ring having a compressed configuration in which the guide bead has an initial position entirely within the lumen of the introducer tube with the tissue bag in the stored position and an expanded configuration upon deployment from the longitudinally extending lumen in which the retaining ring is restricted from reentering the introducer tube, the guide bead being substantially cylindrical with a bore, the cord loop extending through the bore;

a ratchet comprising a pawl having at least one tooth and a rack having a plurality of teeth operationally engaging with the at least one tooth of the pawl, the rack attached to the actuation rod and the pawl pivotally attached to the handle assembly.

20. The tissue retrieval apparatus of claim 19, wherein the ratchet is movable between a first and a second position, the ratchet in the first position arranged to allow the bag to be moved from the stored position to the deployed position as the actuation rod is moved in the distal direction and restricting movement of the actuation rod in the proximal direction, the ratchet in the second position arranged to allow the actuation rod to move in the proximal direction and restricting movement of the actuation rod in the distal direction.

21. The apparatus of claim 20, wherein the ratchet is movable to a third position, the ratchet being in the third position when the pawl is substantially perpendicular to the rack.

22. The apparatus of claim 19 further comprising a handle connected to the cord loop and movable within the lumen of the introducer tube.

* * * * *